(12) United States Patent
Miguel et al.

(10) Patent No.: US 12,409,204 B1
(45) Date of Patent: Sep. 9, 2025

(54) COMPOSITIONS AND METHODS FOR HAIR TREATMENT

(71) Applicant: Neuvian Skincare, LLC, Pinecrest, FL (US)

(72) Inventors: Jacob J. Miguel, Pinecrest, FL (US); Spencer Bouhadir, Lake Worth, FL (US); Jacob A. Miguel, Pinecrest, FL (US)

(73) Assignee: NEUVIAN IP HOLDINGS, LLC, Pinecrest, FL (US)

( * ) Notice: Subject to any disclaimer, the term of this patent is extended or adjusted under 35 U.S.C. 154(b) by 66 days.

(21) Appl. No.: 18/600,574

(22) Filed: Mar. 8, 2024

(51) Int. Cl.
| | |
|---|---|
| *A61K 38/06* | (2006.01) |
| *A61K 45/06* | (2006.01) |
| *A61K 47/10* | (2017.01) |
| *A61K 47/12* | (2006.01) |
| *A61K 47/24* | (2006.01) |
| *A61K 47/36* | (2006.01) |
| *A61K 47/40* | (2006.01) |
| *A61P 17/14* | (2006.01) |

(52) U.S. Cl.
CPC .............. *A61K 38/06* (2013.01); *A61K 45/06* (2013.01); *A61K 47/10* (2013.01); *A61K 47/12* (2013.01); *A61K 47/24* (2013.01); *A61K 47/36* (2013.01); *A61K 47/40* (2013.01); *A61P 17/14* (2018.01)

(58) Field of Classification Search
CPC ......... A61P 17/14; A61K 38/06; A61K 47/24; A61K 47/12; A61K 45/06; A61K 47/10; A61K 47/36; A61K 47/40
See application file for complete search history.

(56) References Cited

U.S. PATENT DOCUMENTS

| | | |
|---|---|---|
| 2014/0309173 A1 | 10/2014 | Dreher |
| 2018/0280481 A1 | 10/2018 | Foger et al. |
| 2021/0154120 A1 | 5/2021 | Kadir et al. |

FOREIGN PATENT DOCUMENTS

| | | | | |
|---|---|---|---|---|
| CN | 110960442 | * | 4/2020 | ............. A61Q 19/08 |
| EP | 1634576 A1 | * | 3/2006 | ............. A61K 8/645 |
| KR | 20180090996 | * | 4/2021 | ......... A61L 26/0057 |
| WO | WO-2014140890 A2 | * | 9/2014 | ......... A61K 31/4172 |

OTHER PUBLICATIONS

KR 20180090996 Machine Translation (Year: 2021).*
CN110960442 Machine Translation (Year: 2020).*
Tamyres Nassa Lima & Carla Aparecida Pedriali Moraes, Bioactive Peptides: Applications and Relevance for Cosmeceuticals, 5 Cosmet. 21 (Year: 2018).*
Loren Pickart & Anna Margolina, Regenerative and Protective Actions of the GHK-Cu Peptide in the Light of New Gene Data, 19 Int'l J Mol. Sci. 1987 (Year: 2018).*
EP1634576 Machine Translation (Year: 2006).*
Sherry Jacob & Anroop Nair, Cyclodextrin Complexes: Perspective from Drug Delivery and Formulation, 79 Drug Dev. Res. 201 (Year: 2018).*
Bellia et al. "Copper(II) complexes with β-cyclodextrin-homocarnosine conjugates and their antioxidant activity," Inorganica Chimica Acta, vol. 360, Issue 3, Feb. 15, 2007, pp. 945-954.
Zoughaib et al. "Enhanced angiogenic effects of RGD, GHK peptides and copper (II) compositions in synthetic cryogel ECM model," Mater Sci Eng C Mater Biol Appl. Jan. 2021: 120:111660.
International Search Report and Written Opinion for PCT/US24/19266 dated Aug. 12, 2024.

* cited by examiner

*Primary Examiner* — Sean M Basquill
(74) *Attorney, Agent, or Firm* — Bryan Cave Leighton Paisner LLP

(57) ABSTRACT

Provided herein are compositions that are useful in treatment of hair conditions comprising (a) a copper-containing peptide; (b) an antioxidant; and (c) a cyclic oligosaccharide-based polymer, where the copper-containing peptide and the antioxidant form a complex. Further provided herein are methods for treatment of hair conditions using the compositions of the disclosure.

26 Claims, 3 Drawing Sheets

(3 of 3 Drawing Sheet(s) Filed in Color)

COMPOSITIONS AND METHODS FOR HAIR TREATMENT

BACKGROUND OF THE INVENTION

There are many recognized forms of hair loss, the most common being alopecia (baldness) wherein human males begin losing scalp hair at the temples and on the crown of the head. Alopecia is a deficiency of either normal or abnormal hair and is primarily a cosmetic problem in humans. While this type of hair loss is largely confined to males, it can be found in women. Despite continuing research, no known cure has yet been found.

The human body is comprised of many different types of hair including terminal hairs, vellus hairs, and modified terminal hairs (such as seen in eye lashes and eyebrows). Terminal hairs are coarse, pigmented, long hairs in which the bulb of the hair follicle is seated deep in the dermis. In contrast, vellus hairs are fine, thin, non-pigmented short hairs in which the hair bulb is located superficially in the dermis. Alopecia is a deficiency of terminal hair, the broad diameter, colored hair that is readily seen. However, in the so-called "bald" person although there is a noticeable absence of terminal hair, the skin does contain vellus hair which is a fine colorless hair which may require microscopic examination to determine its presence. As alopecia progresses, a transition takes place at the balding area wherein the hairs transition from the terminal to the vellus type.

Another factor that contributes to baldness is a change in the cycle of hair growth. All hair, both human and animal, passes through a life cycle that includes three phases: the anagen phase, the catagen phase, and the telogen phase. The anagen phase is the period of active hair growth and, for scalp hair, this phase generally lasts from 3-5 years. The catagen phase is a short transitional phase between the anagen and telogen phases which, in the case of scalp hair, lasts only 1-2 weeks. The final phase is the telogen phase which, for all practical purposes, can be denominated a resting phase where all growth ceases and the hair eventually is shed in preparation for the follicle to grow a new one. Scalp hair in the telogen phase is also relatively short-lived, some 3-4 months elapsing before the hair is shed and a new one begins to grow.

During normal hair growth on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

Alopecia is associated with the severe diminution of hair follicles. A bald human subject will average only about 306 follicles per square centimeter, whereas, a non-bald human in the same age group will have an average of 460 follicles per square centimeter. This amounts to a one-third reduction in hair follicles which, when added to the increased proportion of vellus hair follicles and the increased number of hair follicles in the telogen phase, is both significant and noticeable. Approximately 50% of the hairs must be shed to produce visible thinning of scalp hair. It is thus a combination of factors that produce baldness: transition of hairs from terminal to vellus, increased number of telogen hairs (some of which have been shed), and reduction and loss of hair follicles.

While the progression of male pattern baldness is well studied, very little is known about its cause. The cause is generally believed to be genetic and hormonal in origin although attempts to control it through topical therapies has been only somewhat successful. For example, one of the most commonly used topical hair treatment therapies is minoxidil (Rogaine), which has been used to treat hair loss for decades. Minoxidil, however, generally works well in people with hereditary hair loss at the vertex of the scalp (the area at the back of the head, just under the crown) or for women with general thinning of hair on the top of the scalp, and even then only when applied early. It is unlikely to help people who are already "bald." Furthermore, oral medications, such as finasteride (Propecia) are known to produce significant side effects including lower libido, erectile dysfunction, drowsiness, congestion, and dizziness. Thus, there is an unmet need for topical hair treatment compositions that are effective to prevent or re-grow hair.

SUMMARY OF THE DISCLOSURE

According to some aspects, the present disclosure provides transdermal compositions (and methods of use of transdermal compositions) for topical application that are effective to treat a hair condition, such as baldness, thinning hair, and loss of hair pigmentation. The compositions disclosed herein can be used in a variety of applications, including causing or promoting hair growth and/or hair pigmentation. In some embodiments, the compositions disclosed herein are effective to stimulate the rate of hair growth, stimulate the conversion of vellus hair or intermediate hair to growth as terminal hair, and combinations thereof. In some embodiments, the compositions disclosed herein are effective to prevent hair loss (such as on the scalp), treat hair loss, treat or thicken thinning hair, treat loss of eyebrows, treat loss of eyelashes, promote growth of eyelashes, treat loss of facial or body hair, and combinations thereof. In some embodiments, the compositions disclosed herein are effective to treat all types of alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

According to some aspects, the present disclosure provides a composition for use in treatment of a hair condition comprising: (a) a copper-containing peptide; (b) an antioxidant; and (c) a cyclic oligosaccharide-based polymer, wherein the copper-containing peptide and the antioxidant form a complex. In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine. In some embodiments, the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof. In some embodiments, the cyclic oligosaccharide-based polymer comprises gamma cyclodextrin, optionally a non-crosslinked gamma cyclodextrin. In some embodiments, the composition comprises GHK-Cu peptide, carnosine, and cyclodextrin. In some embodiments, the composition comprises GHK-Cu peptide, L-carnosine, and gamma cyclodextrin. In some embodiments, the complex formed by the copper-containing peptide and the antioxidant is purple in color. In some embodiments, the composition has a pH between 5.5 and 7.3. In some embodiments, the complex formed by the copper-containing peptide and the antioxidant is entrapped by the cyclic oligosaccharide-based polymer.

In some embodiments, the compositions comprises by weight of the total composition: (a) 0.05%-2% copper-containing peptide; (b) 0.5%-10% antioxidant; and (c) 0.1%-20% cyclic oligosaccharide-based polymer. In some embodiments, the compositions comprises by weight of the total composition: (a) 0.05%-2% copper-containing peptide; (b) 0.5%-10% carnosine; and (c) 0.1%-20% cyclodextrin. In some embodiments, the compositions comprises by weight of the total composition: (a) 0.05%-2% GHK-Cu peptide; (b) 0.5%-10% L-carnosine; and (c) 0.1%-20% gamma cyclodextrin. In some embodiments, the compositions comprises at least one pharmaceutically acceptable carrier or excipient. In some embodiments, the composition is a patch, a cream, an ointment, a powder, an aerosol spray, or a hydrogel.

According to some aspects, the present disclosure provides, a method for treating a hair condition in a subject comprising administering to the subject in need thereof a therapeutically effective amount of a composition comprising: (a) a copper-containing peptide; (b) an antioxidant; and (c) a cyclic oligosaccharide-based polymer, wherein the copper-containing peptide and the antioxidant form a complex. In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine. In some embodiments, the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof. In some embodiments, the cyclic oligosaccharide-based polymer comprises gamma cyclodextrin, optionally non-crosslinked gamma cyclodextrin. In some embodiments, the composition comprises GHK-Cu peptide, carnosine, and cyclodextrin. In some embodiments, the composition comprises GHK-Cu peptide, L-carnosine, and gamma cyclodextrin. In some embodiments, the complex formed by the copper-containing peptide and the antioxidant is purple in color. In some embodiments, the composition has a pH between 5.5 and 7.3. In some embodiments, the complex formed by the copper-containing peptide and the antioxidant is entrapped by the cyclic oligosaccharide-based polymer.

In some embodiments, the composition comprises by weight of the total composition: (a) 0.05%-2% copper-containing peptide; (b) 0.5%-10% antioxidant; and (c) 0.1%-20% cyclic oligosaccharide-based polymer. In some embodiments, the composition comprises by weight of the total composition: (a) 0.05%-2% copper-containing peptide; (b) 0.5%-10% carnosine; and (c) 0.1%-20% cyclodextrin. In some embodiments, the composition comprises by weight of the total composition: (a) 0.05%-2% GHK-Cu peptide; (b) 0.5%-10% L-carnosine; and (c) 0.1%-20% gamma cyclodextrin. In some embodiments, the composition further comprises at least one pharmaceutically acceptable carrier or excipient. In some embodiments, the composition is a patch, a cream, an ointment, a powder, an aerosol spray, or a hydrogel.

In some embodiments, the composition is administered topically. In some embodiments, the composition is administered every hour, every two hours, every three hours, every six hours, every twelve hours, every day, every two days, every three days, every five days, every seven days, every ten days, or every fourteen days.

In some embodiments, the hair condition treated by the composition is alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency. In some embodiments, the composition is effective to treat male androgenetic alopecia (male pattern baldness). In some embodiments, the methods disclosed herein further comprise administering a sunscreen.

According to some aspects, the present disclosure provides a composition for altering gene expression of a cell in a human subject comprising: (a) a copper-containing peptide; (b) an antioxidant; and (c) a cyclic oligosaccharide-based polymer, wherein the copper-containing peptide and the antioxidant form a complex; and wherein the composition is effective to decrease the gene expression of one or more of the genes hSDF-1, hAR, hSRD5A1, and hSRD5A3, and/or increase expression of TGF-β2. In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine. In some embodiments, the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof. In some embodiments the cyclic oligosaccharide-based polymer comprises gamma cyclodextrin. In some embodiments, the gamma cyclodextrin is a non-crosslinked gamma cyclodextrin. In some embodiments, the compositions comprises GHK-Cu peptide, carnosine, and cyclodextrin. In some embodiments, the compositions comprises GHK-Cu peptide, L-carnosine, and gamma cyclodextrin. In some embodiments, the complex formed by the copper-containing peptide and the antioxidant is purple in color. In some embodiments, the composition has a pH between 5.5 and 7.3. In some embodiments, the complex formed by the copper-containing peptide and the antioxidant is entrapped by the cyclic oligosaccharide-based polymer.

In some embodiments, the compositions comprises by weight of the total composition: (a) 0.1%-2% copper-containing peptide; (b) 0.5%-10% antioxidant; and (c) 0.1%-20% cyclic oligosaccharide-based polymer. In some embodiments, the compositions comprises by weight of the total composition: (a) 0.1%-2% copper-containing peptide; (b) 0.5%-10% carnosine; and (c) 0.1%-20% cyclodextrin. In some embodiments, the compositions comprises by weight of the total composition: (a) 0.1%-2% GHK-Cu peptide; (b) 0.5%-10% L-carnosine; and (c) 0.1%-20% gamma cyclodextrin. In some embodiments, the compositions comprises at least one pharmaceutically acceptable carrier or excipient.

In some embodiments, the compositions is delivered by a patch, a cream, an ointment, a powder, an aerosol spray, or a hydrogel.

In some embodiments, the composition is effective to treat alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency. In some embodiments, the composition is effective to treat male androgenetic alopecia (male pattern baldness).

According to some aspects, the present disclosure provides a method for altering gene expression of a cell in a human subject comprising the steps of contacting the cell with a composition comprising: (a) a copper-containing peptide; (b) an antioxidant; and (c) a cyclic oligosaccharide-based polymer, wherein the copper-containing peptide and the antioxidant form a complex; and wherein the gene expression is an decrease in one or more of the genes hSDF-1, hAR, hSRD5A1, and hSRD5A3, and/or an increase in expression of TGF-$\beta$2. In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine. In some embodiments, the cyclic oligosaccharide-based polymer comprises alpha cyclodextrin, beta cyclodextrin, gamma cyclodextrin, 2-hydroxypropyl-$\beta$-cyclodextrin, $\beta$-cyclodextrin sulfobutylether, a derivative thereof, or a combination thereof. In some embodiments, the cyclic oligosaccharide-based polymer comprises gamma cyclodextrin. In some embodiments, the gamma cyclodextrin is a non-crosslinked gamma cyclodextrin. In some embodiments, the composition comprises GHK-Cu peptide, carnosine, and cyclodextrin. In some embodiments, the composition comprises GHK-Cu peptide, L-carnosine, and gamma cyclodextrin. In some embodiments, the complex formed by the copper-containing peptide and the antioxidant is purple in color. In some embodiments, the composition has a pH between 5.5 and 7.3. In some embodiments, the complex formed by the copper-containing peptide and the antioxidant is entrapped by the cyclic oligosaccharide-based polymer.

In some embodiments, the composition comprises by weight of the total composition: (a) 0.1%-2% copper-containing peptide; (b) 0.5%-10% antioxidant; and (c) 0.1%-20% cyclic oligosaccharide-based polymer. In some embodiments, the composition comprises by weight of the total composition: (a) 0.1%-2% copper-containing peptide; (b) 0.5%-10% carnosine; and (c) 0.1%-20% cyclodextrin. In some embodiments, the composition comprises by weight of the total composition: (a) 0.1%-2% GHK-Cu peptide; (b) 0.5%-10% L-carnosine; and (c) 0.1%-20% gamma cyclodextrin. In some embodiments, the composition comprises at least one pharmaceutically acceptable carrier or excipient. In some embodiments, the composition is delivered by a patch, a cream, an ointment, a powder, an aerosol spray, or a hydrogel.

In some embodiments, the composition is effective to treat alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency. In some embodiments, the composition is effective to treat male androgenetic alopecia (male pattern baldness).

According to some aspects, the present disclosure provides a kit for treating a hair condition, the kit comprising one or more of the compositions disclosed herein and instructions for use thereof. According to some aspects, the present disclosure provides a kit for altering gene expression of a cell in a human subject, the kit comprising one or more of the compositions disclosed herein and instructions for use thereof.

In some embodiments, the composition comprises a topical formulation suitable for application to the body surface selected from the group consisting of a cream, lotion, spray, solution, gel, ointment, paste, plaster, paint, bioadhesive, suspension, and emulsion. In some embodiments the composition comprises one or more of sunscreen, lotion, balm, shampoo, and moisturizer.

In some embodiments, the composition comprises 2% L-carnosine, 1% L-Histidine HCL, 1% Gamma-cyclodextrin, 0.5% citric acid, 0.2% GHK-copper peptide, 0.2% Zinc PCA, and 0.5% Aromatic alcohol (Benzyl alcohol or Phenoxyethanol).

In some embodiments, the composition comprises 2% carnosine, 1% Histidine HCL, 0.2% GH-copper, 0.5% zinc PCA, 0.5% citric acid, 1% gamma cyclodextrin, 2% glycerin, 10% propanediol, 0.7% phenoxyethanol, 0.1% Ethylhexylglycerin, and 0.5% HA.

In some embodiments, the composition comprises 4% carnosine, 1% Histidine HCL, 0.2% GH-copper, 0.5% zinc PCA, 1% citric acid, 1% gamma cyclodextrin, 2% glycerin, 10% propanediol, 0.7% phenoxyethanol, 0.1% Ethylhexylglycerin, and 0.5% HA.

In some embodiments, citric acid can be exchanged for lactic acid/glycolic acid or similar acids at ranges between 1-3% on average to keep pH within range.

In some embodiments, the composition comprises 0.2-7% carnosine, 0.1-7% Histidine HCL, 0.1-7% Gamma-cyclodextrin, 0.05-5% citric acid, 0.02-3% GHK-copper peptide, 0.02-4% Zinc PCA, 0.05-4% Aromatic alcohol (Benzyl alcohol or Phenoxyethanol), 0-4% glycerin, 0-15% propanediol, 0-1% Ethylhexylglycerin, and 0-5% HA.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Definitions

Figure 2:
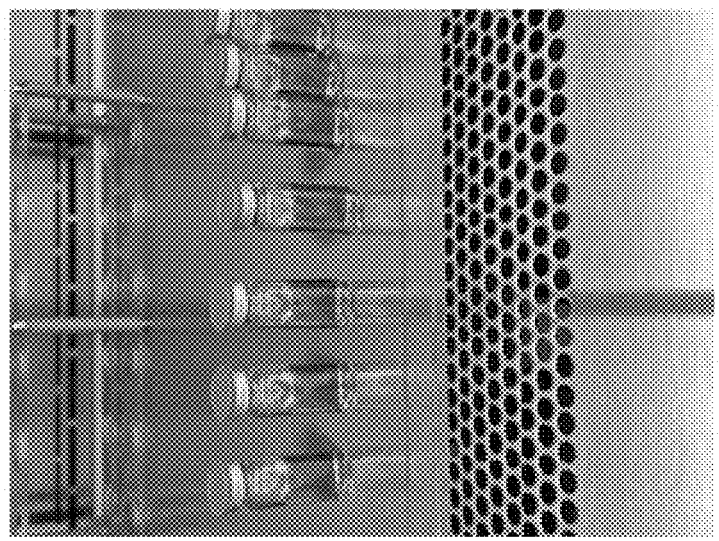
FIG. 2 shows a solution of copper-containing glycyl-L-histidyl-L-lysine copper (GHK-Cu) peptide further comprising zinc PCA that provides a distinctive blue-green color.

The term "about" is used here in conjunction with numeric values to include normal variations in measurements as expected by persons skilled in the art, and is understood have the same meaning as "approximately" and to cover a typical margin of error, such as +5% of the stated value.

Terms such as "a," "an," and "the" are not intended to refer to only a singular entity, but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination y two or more of the listed elements.

Any amounts (e.g., concentrations) of components in a composition given as a percentage (%) refer to a percentage by weight per volume unless otherwise indicated.

As used herein, a "humectant" refers to a substance having an affinity for water and which provides stabilizing action on the water content of a material.

As used herein, the term "nonionic surfactant" refers to a molecule that acts as an uncharged surfactant. Surfactants are chemical compounds that decrease the surface tension or interfacial tension between two liquids, a liquid and a gas, or a liquid and a solid.

As used herein the term "preservative" refers to any known pharmaceutically acceptable preservative that functions by inhibiting bacteria, fungi, yeast, mold, other microbe. Suitable preservatives include but are not limited to antimicrobial agents. In some embodiments, antimicrobial agents comprise sodium benzoate, paraben, benzyl alcohol, sorbic acid, triclosan, phenoxyisopropanol, diazolidinyl urea, bronopol, Alkyl (C12-22) trimethyl ammonium bromide, Alkyl (C12-22) trimethyl ammonium chloride, Benzalkonium chloride, Benzalkonium bromide, Benzalkonium saccharinate, ethylhexylglycerin, phenoxyethanol, or a combination thereof.

As used herein, "subject" refers to any mammal, including humans, domestic and farm animals, and zoo, sports, or pet animals, such as dogs, horses, cats, sheep, pigs, cows, etc. The preferred subject herein is a human subject, including adults, children, and the elderly.

The term "topical" application refers to application to skin, dermis or tissue site, and application to such tissue sites may include application adjacent to or within the tissue site.

The terms "treat," "treated," or "treating" as used herein refers to therapeutic treatment, cosmetic treatment and/or prophylactic or preventative measures, wherein the object is to prevent or slow down (lessen) an undesired physiological condition, disorder or disease, or to obtain beneficial or desired clinical results. As used herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

As used herein, the term a "therapeutically effective amount" is an amount sufficient to effect beneficial or desired results. A therapeutically effective amount can be administered in one or more doses. The therapeutically effective amount is generally determined by a physician on a case-by-case basis and is within the skill of one in the art. Several factors are typically taken into account when determining an appropriate dosage. These factors include age, sex and weight of the patient, the condition being treated, the severity of the condition and the form of the composition being administered.

Compositions

According to some aspects, the present disclosure provides transdermal compositions (and methods of use of transdermal compositions) for topical application that are effective to treat a hair condition, such as baldness, thinning hair, and loss of hair pigmentation. The compositions disclosed herein can be used in a variety of applications, including causing or promoting hair growth and/or hair pigmentation. In some embodiments, the compositions disclosed herein are effective to stimulate the rate of hair growth, stimulate the conversion of vellus hair or intermediate hair to growth as terminal hair, stimulate pigmentation of hairs, and combinations thereof. In some embodiments, the compositions disclosed herein are effective to prevent hair loss (such as on the scalp), treat hair loss, treat or thicken thinning hair, treat loss of eyebrows, treat loss of eyelashes, promote growth of eyelashes, treat loss of facial or body hair, and combinations thereof. In some embodiments, the compositions disclosed herein are effective to treat all types of alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

The composition disclosed herein can take the form of a gel, a cream, a lotion, an ointment, a solution, a solid "stick," etc., that can be rubbed or sprayed onto the skin, e.g., the scalp, or other suitable portion of the skin. In some aspects, the present disclosure provides methods of using such compositions and kits including such compositions.

According to some aspects, the present disclosure provides a composition as disclosed herein that is used to treat various hair related conditions such as those described herein. The compositions of the present disclosure can be used to treat any disorder, disease, or condition that would benefit from an agent that promotes hair growth and/or hair pigmentation. In some embodiments, the compositions disclosed herein are effective to slow, prevent, or reverse transition of hairs from terminal to vellus; decrease the number of telogen hairs; slow, prevent, or reverse loss of hair follicles; or combinations thereof.

In some aspects, the present disclosure provides a delivery system that is effective to penetrate human skin. In some embodiments, the delivery system comprises a penetration-enhancing agent and/or surfactant ingredient or combinations thereof. In certain embodiments, the delivery system is effective to transport one or more active ingredients into the epidermis or dermis.

According to some aspects, the present disclosure provides a hair treatment composition comprising: (a) a copper-containing peptide; (b) an antioxidant; and (c) a cyclic oligosaccharide-based polymer, wherein the copper-containing peptide and the antioxidant form a complex. In some embodiments, the composition is effective to cause a decrease in expression of one or more of the genes hSDF-1, hAR, hSRD5A1, and hSRD5A3, and/or an increase in expression of the gene TGF-β2.

In some embodiments, the copper-containing peptide comprises glycyl-L-histidyl-L-lysine copper (GEM-Cu) peptide. In some embodiments, the hair treatment composition comprises by weight of the total composition, 0.05%-2% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) of copper-containing peptide. In some embodiments, the hair treatment composition comprises, by weight of the total composition, 0.05%-2% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) GHK-Cu peptide.

In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises carnosine. In some embodiments, the antioxidant comprises anserine. In some embodiments, the antioxidant comprises L-carnosine. In some embodiments, the hair treatment composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) antioxidant. In some embodiments, the hair treatment composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) carnosine. In some embodiments, the hair treatment composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) L-carnosine.

In some embodiments, the hair treatment composition comprises GHK-Cu peptide, carnosine, and cyclodextrin. In some embodiments, the hair treatment composition comprises comprising GHK-Cu peptide, L-carnosine, and gamma cyclodextrin.

In some embodiments, the cyclic oligosaccharide-based polymer comprises an alpha cyclodextrin, beta cyclodextrin, a gamma cyclodextrin, a 2-hydroxypropyl-β-cyclodextrin, a β-cyclodextrin sulfobutylether, hydroxyethyl-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-1-β-cyclodextrin, glocosyl-β-cyclodextrin, maltosyl-β-cyclodextrin or any derivative thereof, and any combination thereof. In some embodiments, the cyclic oligosaccharide-based polymer is non-crosslinked. In some embodiments, the cyclic oligosaccharide-based polymer is crosslinked. In some embodiments, the cyclic oligosaccharide-based polymer is an alkylated derivative. In some embodiments, the hair treatment composition comprises, by weight of the total composition, 0.1%-30% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30% or any value therebetween) cyclic oligosaccharide-based polymer. In some embodiments, the hair treatment composition comprises, by weight of the total composition, 0.1%-30% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30% or any value therebetween) cyclodextrin or an alkylated derivative thereof. In some embodiments, the hair treatment composition comprises, by weight of the total composition, 0.1%-30% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30% or any value therebetween) gamma cyclodextrin or an alkylated derivative thereof.

In some embodiments, the cyclic oligosaccharide-based polymer comprises gamma cyclodextrin. In some embodiments, the gamma cyclodextrin comprises non-crosslinked gamma cyclodextrin. In some embodiments, the gamma cyclodextrin comprises crosslinked gamma cyclodextrin.

In some embodiments, the alpha cyclodextrin has the following chemical formula:

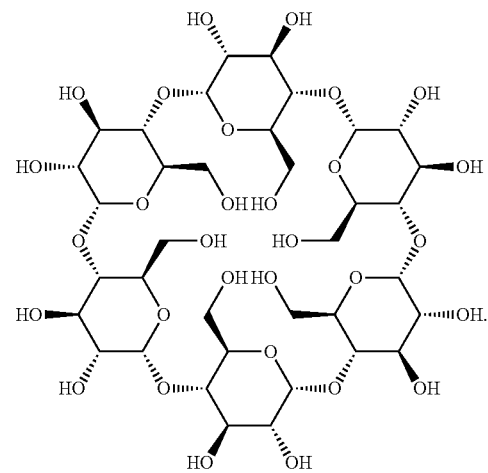 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]1[C@H](O)[C@H]2O)O[C@@H]7CO)O[C@@H]6CO)O[C@@H]5CO)O[C@@H]4CO)O[C@@H]3CO]

In some embodiments, the beta cyclodextrin has the following chemical formula:

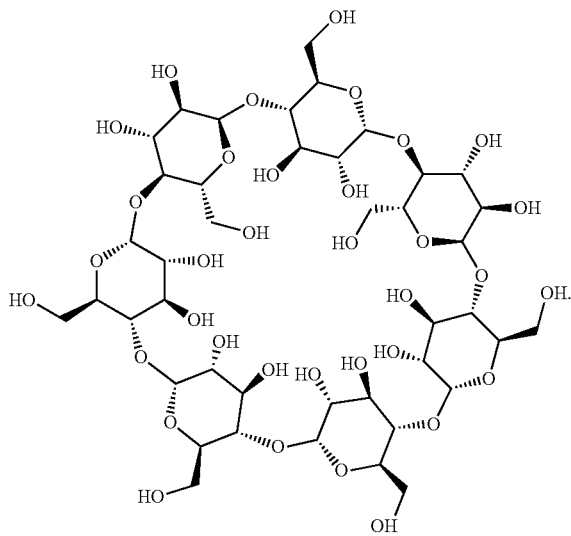 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]1[C@H](O)[C@H]2O)O[C@@H]8CO)O[C@@H]7CO)O[C@@H]6CO)O[C@@H]5CO)O[C@@H]4CO)O[C@@H]3CO]

In some embodiments, the gamma cyclodextrin has the following chemical formula:

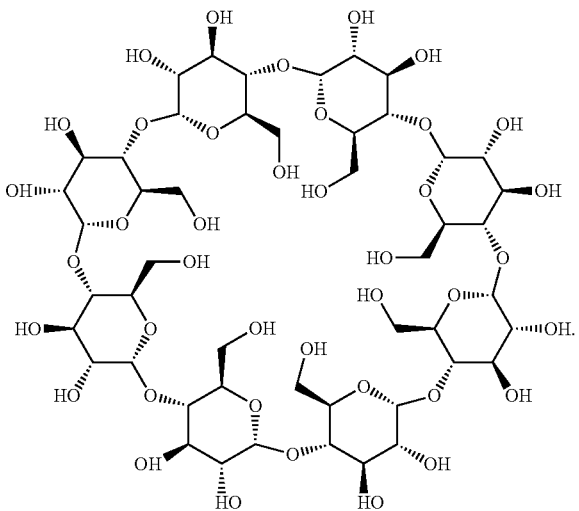 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]9[C@H](O)[C@@H](O)[C@@H](O[C@H]1[C@H](O)[C@H]2O)O[C@@H]9CO)O[C@@H]8CO)O[C@@H]7CO)O[C@@H]6CO)O[C@@H]5CO)O[C@@H]4CO)O[C@@H]3CO]

Figure 1:
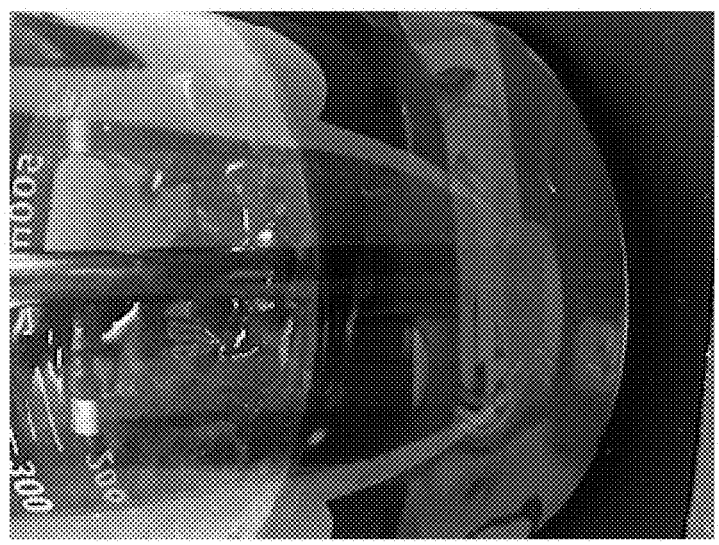
FIG. 1 shows an exemplary hair treatment composition comprising copper with distinctive blue color (i.e. solution of copper-containing glycyl-L-histidyl-L-lysine copper (GHK-Cu) peptide).

In some embodiments, the complex formed by the copper-containing peptide and the antioxidant is purple in color, while the copper-containing peptide is blue in color (FIG. 1). In some embodiments, the complex formed by GHK-Cu peptide and carnosine is purple in color. In some embodiments, the complex formed by GHK-Cu peptide and L-carnosine is purple in color. In some embodiments, the addition of zinc PCA produces a blue-green color (FIG. 2).

In some embodiments, the composition has a pH between 5.5 and 7.3 (e.g., pH 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3 or any value therebetween). In some embodiments, the composition has a pH between band 7 (e.g., pH 6, 6.1, 6.2, 6.3, 6.4, 6.5, 6.6, 6.7, 6.8, 6.9, 7, or any value therebetween).

In some embodiments, the copper-containing peptide is entrapped by the cyclic oligosaccharide-based polymer. In some embodiments, the GHK-Cu peptide is entrapped by cyclodextrin. In some embodiments, the GHK-Cu peptide is entrapped by gamma cyclodextrin. In some embodiments, the complex formed by the copper-containing peptide and the antioxidant is entrapped by the cyclic oligosaccharide-based polymer. In some embodiments, the complex formed by GHK-Cu peptide and carnosine is entrapped by cyclodextrin. In some embodiments, the complex formed by GHK-Cu peptide and L-carnosine is entrapped by gamma cyclodextrin.

In some embodiments, the hair treatment composition comprises by weight of the total composition: (a) 0.05%-2% copper-containing peptide (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween); (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) antioxidant; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclic oligosaccharide-based polymer.

In some embodiments, the hair treatment composition comprises by weight of the total composition: (a) 0.05%-2% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) copper-containing peptide; (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) carnosine; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclodextrin.

In some embodiments, the hair treatment composition comprises by weight of the total composition: (a) 0.05%-2% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) GHK-Cu peptide; (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) L-carnosine; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) gamma cyclodextrin.

In some embodiments, the hair treatment composition further comprises at least one pharmaceutically acceptable carrier or excipient.

In some embodiments, the hair treatment composition further comprises at least one of: a pH buffer; a humectant; a nonionic surfactant; and a preservative.

In some embodiments, the hair treatment composition comprises 0.05%-3% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3%, or any value therebetween) pH buffer. In some embodiments, the hair treatment composition comprises 3%-30% (e.g., 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30%, or any value therebetween) humectant. In some embodiments, the hair treatment composition comprises 5%-15% (5, 5.5, 6, 6.5, 7, 7.5, 8, 8.5, 9, 9.5, 10, 10.5, 11, 11.5, 12, 12.5, 13, 13.5, 14, 14.5, 15%, or any value therebetween) nonionic surfactant. In some embodiments, the hair treatment composition comprises 0.05%-1.5% (e.g., 0.05, 0.1, 0.2, 0.3, 0.4, 0.5, 0.6, 0.7, 0.8, 0.9, 1, 1.1, 1.2, 1.3, 1.4, 1.5, or any value therebetween) preservative.

In some embodiments, the pH buffer comprises at least one of citric acid, magnesium citrate, magnesium sulfate, sodium citrate or sodium sulfate. In some embodiments, the pH buffer comprises citric acid.

In some embodiments, the humectant comprises at least one of an amino acid, aloe vera extract, a fatty acid, hyaluronic acid (HA), collagen, silicone, a disaccharide (e.g., sucrose or trehalose), maltitol, erythrol, sorbitol, glycerin, propanediol, propylene glycol, glycerin or any other glycol/diol. In some embodiments, the humectant comprises glycerin and/or HA. In some embodiments, HA is swapped for any other heavy molecular weight polymer such as collagen or a derivative thereof. In some embodiments, collagen is interchangeable with HA or can be combined with HA, e.g., 0.6% HA combined with 0.5% collagen. In some embodiments, the composition comprises 0.2-5% of HA, 0.2-5% of collagen or derivatives thereof, or 0.2-5% of HA and collagen or a derivative thereof combined. In some embodiments, the hair treatment composition comprises 3-30% (e.g., 3, 4, 5, 6, 7, 8, 9, 10, 11, 12, 13, 14, 15, 16, 17, 18, 19, 20, 21, 22, 23, 24, 25, 26, 27, 28, 29, 30% or any number therebetween) of propanediol, propylene glycol, glycerin or any other glycol/diol, or a combination thereof.

In some embodiments, the nonionic surfactant comprises at least one of tearyl alcohol, cetearyl alcohol, or a combination of both. In some embodiments, the nonionic surfactant comprises tearyl alcohol. In some embodiments, the nonionic surfactant comprises cetearyl alcohol. In some embodiments, the hair treatment composition comprises 3-30% of a nonionic surfactant.

In some embodiments, the preservative comprises at least one of sodium benzoate, paraben, benzyl alcohol, sorbic acid, triclosan, phenoxyisopropanol, diazolidinyl urea, bronopol, Alkyl (C12-22) trimethyl ammonium bromide, Alkyl (C12-22) trimethyl ammonium chloride, Benzalkonium chloride, Benzalkonium bromide, Benzalkonium saccharinate, ethylhexylglycerin, or phenoxyethanol. In some embodiments, the preservative comprises phenoxyethanol or ethylhexylglycerin or both, optionally at 0.05%-1.5% of the composition. In some embodiments, the phenoxyethanol or ethylhexylglycerin can be swapped for parabens or other aromatic alcohols such as benzyl alcohol, optionally at 0.05%-1.5% of the composition.

In some embodiments, the hair treatment composition further comprises at least one of the following constituents: sunflower oil, Tegomuls 90 S, cetyl alcohol, cetyl palmitate, Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

In some embodiments, the hair treatment composition further comprises at least one constituent selected from the group consisting of an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

In some embodiments, the composition is lyophilized. In some embodiments, the composition is spray dried to form a sterile powder. In some embodiments, the composition is freeze dried onto a patch.

In some embodiments, the hair treatment composition is a patch, a cream, an ointment, a powder, an aerosol spray, or a hydrogel. In some embodiments, the hair treatment composition is impregnated into a dressing.

According to certain embodiments, the compositions disclosed herein are in a topical formulation suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter.

Topical formulations include those in which any other active ingredient(s) is (are) dissolved or dispersed in a dermatological vehicle known in the art (e.g., aqueous or nonaqueous gels, ointments, water-in-oil or oil-in-water emulsions). Constituents of such vehicles can comprise water, aqueous buffer solutions, non-aqueous solvents (e.g., ethanol, isopropanol, benzyl alcohol, 2-(2-ethoxyethoxy) ethanol, propylene glycol, propylene glycol monolaurate, glycofurol or glycerol), oils (e.g., a mineral oil such as a liquid paraffin, natural or synthetic triglycerides, or silicone oils such as dimethicone). Depending, inter alia, upon the nature of the formulation as well as its intended use and site of application, the dermatological vehicle employed can contain one or more components (e.g., when the formulation is an aqueous gel, components in addition to water) selected from the following list: a solubilizing agent or solvent (e.g., a β-cyclodextrin, such as bydroxypropyl, or an alcohol or polyol such as ethanol, propylene glycol or glycerol); a thickening agent (e.g., hydroxyethylceliulose, hydroxypropylcellulose, carboxymethylcellulose or carbomer); a gelling agent (e.g., a polyoxyethylene-polyoxypropylene copolymer); a preservative (e.g., benzyl alcohol, benzalkonium chloride, chlorhexidine, chlorbutol, a benzoate, potassium sorbate or EDTA or salt thereof); and pH buffering agent(s) (e.g., a mixture of dihydrogen phosphate and hydrogen phosphate salts, or a mixture of citric acid and a hydrogen phosphate salt).

A pharmaceutically acceptable carrier can also be incorporated in the formulation of the present disclosure and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers. The term "pharmaceutically acceptable" or "pharmaceutically acceptable carrier" is used herein to refer to a compound or composition that can be incorporated into a pharmaceutical formulation without causing undesirable biological effects or unwanted, interaction with other components of the formulation. "Carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin.

According to certain embodiments, the formulations disclosed herein may comprise a film former. A film former, when it dries, forms a protective film over the site of application. The film former inhibits removal of the active ingredient and keeps it in contact with the site being treated. An example of a film former is Flexible Collodion, US P. As described in Remington: The Science and Practice of Pharmacy, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former can act additionally as a carrier. Solutions that dry to form a film are sometimes referred to as paints. Creams, as is well known in the arts of pharmaceutical formulation, are viscous liquids or semisolid emulsions, either oil-in-water or water-in-oil.

Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and in some embodiments, comprise a liquid oily emulsion of the oil-in-water type. In some embodiments, lotion formulations are used herein for treating large body areas, because of the ease of applying a more fluid composition. It is generally necessary that the insoluble matter in a lotion be finely-divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize, or preserve the solute. Common examples of solvents used in preparing solutions are ethanol, water, propylene glycol or any other acceptable vehicles. As is well known, gels are semisolid, suspension-type systems. Single-phase gels contain organic macromolecules distributed substantially uniformly throughout the carrier liquid, which is typically aqueous, but also, in some embodiments, contains an alcohol, and, optionally, an oil. In some embodiments, "organic macromolecules," are used, i.e., gelling agents, are cross-linked acrylic acid polymers such as the "carbomer" family of polymers, e.g., carboxypolyalkylenes that can be obtained commercially under the Carbopol trademark. In other embodiments, hydrophilic polymers are used such as polyethylene oxides, polyoxyethylene-polyoxypropylene copolymers and polyvinylalcohol; cellulosic polymers such as hydroxy-propyl cellulose, hydroxyethyl cellulose, hydroxypropyl methylcellulose, hydroxy-propyl methylcellulose phthaiate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19$^{th}$ Ed. (Easton, Pa.: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum.

Enhancers are those lipophilic co-enhancers typically referred to as "plasticizing" enhancers, i.e., enhancers that have a molecular weight in the range of about 150 to 1000, an aqueous solubility of less than about 1 wt. %, in some embodiments less than about 0.5 wt. %, and most in some embodiments less than about 0.2 wt. %. The Hildebrand solubility parameter 6 of plasticizing enhancers is in the range of about 2.5 to about 10, in some embodiments in the range of about 5 to about 10. In some embodiments lipophilic enhancers are fatty esters, fatty alcohols, and fatty ethers. Examples of specific fatty acid esters include methyl laurate, ethyl oleate, propylene glycol nionolaurace, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, in some embodiments, a $C_2$-$C_4$ alkane diol or triol, are substituted with one or two fatty ether substituents. Additional permeation enhancers will be known to those of ordinary skill in the art of topical drug delivery, and/or are described in the pertinent texts and literature. See, e.g., Percutaneous Penetration Enhancers, eds. Smith et al. (CRC Press, 1995)(incorporated herein by reference).

Various other additives can be included in the compositions of the present disclosure in addition to those identified above. These include, but are not limited to, antioxidants, astringents, perfumes, preservatives, emollients, pigments, dyes, humectants, propeliants, and sunscreen agents, as well as other classes of materials whose presence can be pharmaceutically or otherwise desirable. Typical examples of optional additives for inclusion in the formulations of the disclosure are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), β-tocopherol, gamma-tocopherol, delta-tocopherol, epsilon-tocopherol, zeta-tocopherol, Z GAMMA-tocopherol, eta-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), beta-tocopherol, gamma-tocopherol, delta-tocopherol, epsilon-tocopherol, zeta-tocopherol, zeta 2-tocopherol, eta-tocopherol, and retinol (Vitamin A), and/or pharmaceutically acceptable salts, esters, amides, or other derivatives thereof. In some embodiments the tocopherol compound is a-tocopherol. Additional agents include those that are capable of improving oxygen supply in skin tissue, as described, for example, in Gross, et al, WO 94/00098 and Gross, et al, WO 94/00109, both assigned to Lancaster Group AG (incorporated herein by reference). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycmnamate, octyl salicylate, oxybenzone, padirnate O, phenylbenzirmdazole sulfonic acid, sulisobenzone, titanium dioxide, trolamine salicylate, zinc oxide, ensulizole, meradiraate, octinoxate, octisalate, and octocrylene. See, Title 21. Chapter 1. Subchapter D. Part 352. "Sunscreen drug products for over-the-counter human use" incorporated herein in its entirety.

Other embodiments can include a variety of non-carcinogenic, non-irritating materials that facilitate treatment with the formulations of the disclosure. Such materials can include nutrients, minerals, vitamins, electrolytes, enzymes, herbs, plant extracts, glandular or animal extracts, or safe therapeutic agents that can be added to the formulation to facilitate the treatment of a hair condition. The amounts of these various additives are those conventionally used in the cosmetics field, and range, for example, from about 0.01% to about 20% of the total weight of the topical formulation.

The formulations of the disclosure can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds.

The formulations can also contain irritation-mitigating additives to minimize or eliminate the possibility of skin irritation or skin damage resulting from the chemical entity to be administered, or other components of the composition. Suitable irritation-mitigating additives include, for example: a-tocopherol; monoamine oxidase inhibitors, particularly phenyl alcohols such as 2-phenyl-1-ethanol; glycerin; salicylates; ascorbates; ionophores such as monensin; amphophilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation.

Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites. Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycmnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil.

A cream, lotion, gel, ointment, paste or the like can be spread on the affected surface and gently rubbed in. A solution can be applied in the same way, but more typically will be applied with a dropper, swab, or the like, and carefully applied to the affected areas.

The pharmaceutical compositions of the disclosure comprise one or more active ingredients, e.g. therapeutic agents, in admixture with one or more pharmaceutically-acceptable diluents or carriers and, optionally, one or more other compounds, drugs, ingredients and/or materials. Regardless of the route of administration selected, the agents/compounds of the present disclosure are formulated into pharmaceutically-acceptable dosage forms by conventional methods known to those of skill in the art. See, e.g., Remington, The Science and Practice of Pharmacy ($21^{st}$ Edition, Lippincott Williams and Wilkins, Philadelphia, Pa.). In some embodiments, the compositions disclosed herein further comprise additional therapeutic agents selected from the group consisting of minoxidil, Finasteride, and ketoconazole.

Pharmaceutically acceptable diluents or carriers are well known in the art (see, e.g., Remington, The Science and Practice of Pharmacy ($21^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, 33ecompleme, etc. Each pharmaceutically acceptable diluent or carrier used in a pharmaceutical composition of the disclosure must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the disclosure may, optionally, contain additional ingredients and/or materials commonly used in pharmaceutical and/or over-the-counter compositions. These ingredients and materials are well known in the art and non-limiting examples include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Dosage forms for the topical or transdermal administration include powders, sprays, ointments, pastes, creams, lotions, gels, solutions, patches, and drops. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

In some embodiments, the compositions disclosed herein may be combined with an active drug substance that is potentially irritating to a subject's skin, such as alpha hydroxy acids, retinoic acids, benzoyl peroxide, calcipotriene, calcineurin inhibitors, sunscreens, sunblocks, bleaching agents, 35ecomplement, antiperspirants, or combinations thereof. In some embodiments, the active drug substance may be anti-rosacea agents such as metronidazole, precipitated sulfur, sodium sulfacetamide, or azelaic acid; antibacterial agents (antibiotics) such as clindamycin phosphate, erythromycin, or antibiotics from the tetracycline family; antimycobacterial agents such as dapsone; other antiacne agents such as retinoids, or benzoyl peroxide; antiparasitic agents such as metronidazole, permethrin, crotamiton, thiabendazole, ivermectin or pyrethroids; antifungal agents such as compounds of the imidazole family such as miconazole, clotrimazole, econazole, ketoconazole, or salts thereof, polyene compounds such as amphotericin B, compounds of the allylamine family such as terbinafine.

In some embodiments, the compositions disclosed herein may comprise additional anti-inflammatory agents, such as steroidal anti-inflammatory agents including hydrocortisone triamcinolone, fluocinonide, betamethasone valerate or clobetasol propionate, or non-steroidal anti-inflammatory agents such as ibuprofen and salts thereof, naproxen and salts thereof, or acetaminophen. In some embodiments, the compositions disclosed herein may comprise anesthetic agents such as the "amide" and "ester" anesthetics such as lidocaine, prilocaine, tetracaine, hydrochloride and derivatives thereof. In some embodiments, the compositions disclosed herein may comprise antipruriginous agents such as thenaldine, trimeprazine, or pramoxine. In some embodiments, the compositions disclosed herein may comprise antiviral agents such as acyclovir. In some embodiments, the compositions disclosed herein may comprise keratolytic agents such as alpha- and beta-hydroxy acids such as glycolic acid or salicylic acid, or urea. In some embodiments, the compositions disclosed herein may comprise anti-free radical agents (antioxidants) such as Vitamin E (alpha tocopherol) and its derivatives, Vitamin C (ascorbic acid), Vitamin A (retinol) and its derivatives, and superoxide dismutases. In some embodiments, the compositions disclosed herein may comprise antiseborrheic agents such as zinc pyrithione and selenium sulfide. In some embodiments, the compositions disclosed herein may comprise antihistamines such as cyproheptadine or hydroxyzine. In some embodiments, the compositions disclosed herein may comprise antipsoriatic agents such as calcipotriene, anthralines, coal tar. In some embodiments, the compositions disclosed herein may comprise immune modulating agents such as imiquimod. In some embodiments, the compositions disclosed herein may comprise calcineurin inhibitors pimecrolimus and tacrolimus.

In some embodiments, the composition comprises 2% L-carnosine, 1% L-Histidine HCL, 1% Gamma-cyclodextrin, 0.5% citric acid, 0.2% GHK-copper peptide, 0.2% Zinc PCA, and 0.5% Aromatic alcohol (Benzyl alcohol or Phenoxyethanol).

In some embodiments, the composition comprises 2% carnosine, 1% Histidine HCL, 0.2% GH-copper, 0.5% zinc PCA, 0.5% citric acid, 1% gamma cyclodextrin, 2% glycerin, 10% propanediol, 0.7% phenoxyethanol, 0.1% Ethylhexylglycerin, and 0.5% HA.

In some embodiments, the composition comprises 4% carnosine, 1% Histidine HCL, 0.2% GH-copper, 0.5% zinc PCA, 1% citric acid, 1% gamma cyclodextrin, 2% glycerin, 10% propanediol, 0.7% phenoxyethanol, 0.1% Ethylhexylglycerin, and 0.5% HA.

In some embodiments, citric acid can be exchanged for lactic acid/glycolic acid or similar acids at ranges between 1-3% on average to keep pH within range.

Methods for Treating a Hair Condition

According to certain aspects the compositions such as those described herein can be administered to a subject, such as a human subject, by applying to the skin of the subject, e.g., in areas located at or at least within the vicinity of a desired target area. According to some aspects, the present disclosure provides methods of administering any composition such as discussed herein to a subject. In some embodiments, the compositions are applied in a therapeutically effective, pharmaceutically acceptable amount as a pharmaceutically acceptable formulation. Any of the compositions disclosed herein may be administered to the subject in a therapeutically effective dose. When administered to a subject, effective amounts will depend on the particular condition being treated and the desired outcome. A therapeutically effective dose may be determined by those of ordinary skill in the art, for instance, employing factors such as those described herein and using no more than routine experimentation. In some embodiments, a therapeutically effective dose is determined to be the dose necessary to promote hair growth or hair pigmentation in a subject so as to achieve a desirable look or appearance. In some embodiments, a therapeutically effective dose is determined to be a dose necessary to promote hair growth as measured in terms hair density, hair diameter, hair growth rate, or anagen/telogen ratio, e.g., by methods described herein utilizing digital images of a subjects hair taken over time and analyzed by certain software (e.g., TRICHOSCAN®).

According to some embodiments, the compositions disclosed herein can be applied as sequential administration over a certain time period, such as hours, days, weeks, months, or years. This may be accomplished, for example, by repeated administrations of a composition of the invention by one or more of the methods described herein, or by a sustained or controlled release delivery system in which the composition is delivered over a prolonged period without repeated administrations. Administration of the composition using such a delivery system may be, for example, by a transdermal patch. Maintaining a substantially constant concentration of the composition may be preferred in some cases.

In some embodiments, a composition as disclosed herein may be applied to the skin at a relatively high concentration during an initial treatment, and the amount of composition may be lowered or "titrated" down to a relatively lower concentration maintenance dose or amount. A composition as disclosed herein can be used to promote hair growth and/or hair pigmentation. In some embodiments, the compositions disclosed herein may be used for certain treatments of hair loss and/or loss of hair pigmentation, e.g., baldness and/or greying of the hair. In some embodiments, the application of the composition is effective to provide gradual improvement after one application or with successive applications.

According to some embodiments, the compositions disclosed herein can be used in combination therapy with one or more additional therapeutic agents. For combination treatment with more than one active agent, where the active agents are in separate dosage formulations, the active agents may be administered separately or in conjunction. In some embodiments, the administration of one element may be prior to, concurrent to, or subsequent to the administration of the other agent. In some embodiments, the additional therapeutic agent is present in a provided composition in addition to the compositions disclosed herein. In other embodiments, the additional therapeutic agent is administered separately from the compositions disclosed herein. In some embodiments, the additional therapeutic agents are selected from the group consisting of minoxidil, Finasteride, and ketoconazole.

In some embodiments, a composition as disclosed herein, and an additional therapeutic agent are each administered in an effective amount (i.e., each in an amount which would be therapeutically effective if administered alone). In some embodiments, a composition as disclosed herein and the additional therapeutic agent are each administered in an amount which alone does not provide a therapeutic effect (a sub-therapeutic dose). In yet other embodiments, a composition as disclosed herein can be administered in an effective amount, while the additional therapeutic agent is administered in a sub-therapeutic dose. In still other embodiments, a composition as disclosed herein can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms "in combination" or "co-administration" do not restrict the order in which therapies (e.g., prophylactic and/or therapeutic agents) are administered to a subject.

In some embodiments, co-administration encompasses administration of the first and second amounts of the compounds in an essentially simultaneous manner, such as in a single pharmaceutical composition, for example, cream or spray having a fixed ratio of first and second amounts, or in multiple, separate creams or sprays for each. In addition, such co-administration also encompasses use of each compound in a sequential manner in either order. When co-administration involves the separate administration of the first amount of a composition as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined by taking into account the properties of each compound. For example, a composition as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

In some embodiments, a first therapy (e.g., a prophylactic or therapeutic agent such as a composition disclosed herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In some embodiments, a composition such as disclosed herein may be applied to the skin of a subject, e.g., at any suitable location. The composition may be contacted using any suitable method. For example, the composition may be rubbed on, poured on, applied with an applicator (e.g., a gauze pad, a swab, a bandage, etc.), or the like. In some cases, the composition can be a liquid, a gel, a cream, a lotion, an ointment, a solid "stick," or the like, that can be applied to the skin by hand, for example, by rubbing or spraying.

Also disclosed herein are compositions and methods for topical applications for maintaining hair growth, preventing loss of hair, regrowing lost hair, maintaining hair color, preventing loss of hair color, and regaining lost hair color. As used herein, topical application, topical administration, and topically administering are used interchangeably and include the administration of a composition to the upper and/or lower eyelid margin, eyebrow region, scalp, face, body, and combinations thereof. Topical application or administering results in the delivery of an active agent to a localized region of the body. In some embodiments, the methods and compositions disclosed herein are effective to slow, prevent, or reverse transition of hairs from terminal to vellus; decrease the number of telogen hairs; slow, prevent, or reverse loss of hair follicles; or combinations thereof.

Another aspect of the disclosure is directed to a method for treating a hair condition in a subject comprising administering to the subject in need thereof a hair treatment composition comprising: (a) a copper-containing peptide; (b) an antioxidant; and (c) a cyclic oligosaccharide-based polymer, wherein the copper-containing peptide and the antioxidant form a complex. In some embodiments, the composition is effective to cause a decrease in expression of one or more of the genes hSDF-1, hAR, hSRD5A1, and hSRD5A3, and/or an increase in expression of the gene TGF-β2.

In some embodiments, the copper-containing peptide comprises glycyl-L-histidyl-L-lysine copper (GEM-Cu) peptide. In some embodiments, the composition comprises, by weight of the total composition, 0.05%-2% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) of copper-containing peptide. In some embodiments, the composition comprises, by weight of the total composition, 0.05%-2% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) GHK-Cu peptide.

In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises carnosine. In some embodiments, the antioxidant comprises anserine. In some embodiments, the antioxidant comprises L-carnosine. In some embodiments, the composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) antioxidant. In some embodiments, the composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) carnosine. In some embodiments, the composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) L-carnosine.

In some embodiments, the composition comprises GHK-Cu peptide, carnosine, and cyclodextrin. In some embodiments, the composition comprises GHK-Cu peptide, L-carnosine, and gamma cyclodextrin.

In some embodiments, the cyclic oligosaccharide-based polymer comprises an alpha cyclodextrin, beta cyclodextrin, a gamma cyclodextrin, a 2-hydroxypropyl-β-cyclodextrin, a β-cyclodextrin sulfobutylether, hydroxyethyl-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-1-β-cyclodextrin, glocosyl-β-cyclodextrin, maltosyl-β-cyclodextrin or any derivative thereof, and any combination thereof. In some embodiments, the cyclic oligosaccharide-based polymer is non-crosslinked. In some embodiments, the cyclic oligosaccharide-based polymer is crosslinked. In some embodiments, the cyclic oligosaccharide-based polymer is an alkylated derivative. In some embodiments, the composition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclic oligosaccharide-based polymer. In some embodiments, the hair treatment composition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclodextrin or an alkylated derivative thereof. In some embodiments, the hair treatment composition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) gamma cyclodextrin or an alkylated derivative thereof.

In some embodiments, the cyclic oligosaccharide-based polymer comprises gamma cyclodextrin. In some embodiments, the gamma cyclodextrin comprises non-crosslinked gamma cyclodextrin. In some embodiments, the gamma cyclodextrin comprises crosslinked gamma cyclodextrin.

In some embodiments, the alpha cyclodextrin has the following chemical formula:

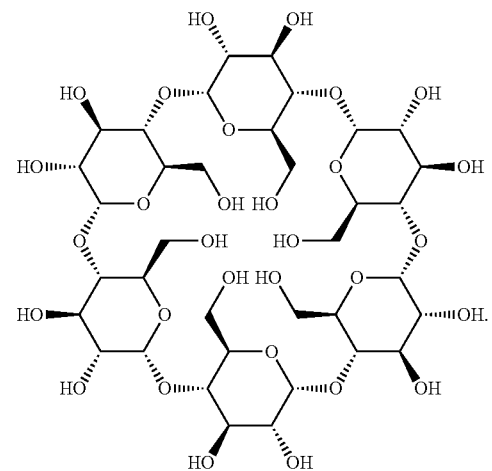 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]1[C@H](O)[C@H]2O)O[C@@H]7CO)O[C@@H]6CO)O[C@@H]5CO)O[C@@H]4CO)O[C@@H]3CO]

In some embodiments, the beta cyclodextrin has the following chemical formula:

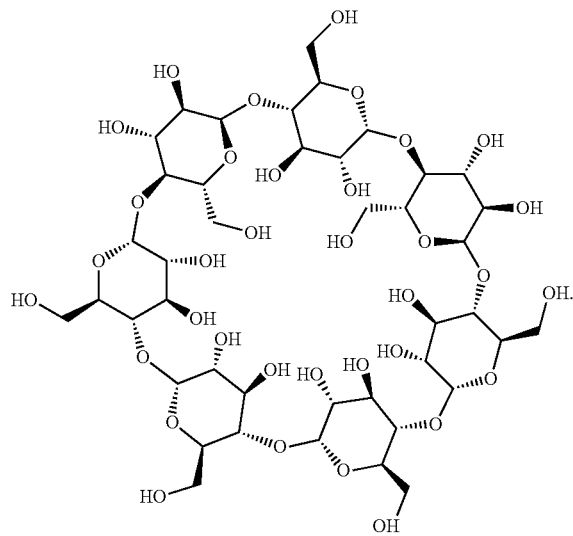 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]1[C@H](O)[C@H]2O)O[C@@H]8CO)O[C@@H]7CO)O[C@@H]6CO)O[C@@H]5CO)O[C@@H]4CO)O[C@@H]3CO]

In some embodiments, the gamma cyclodextrin has the following chemical formula:

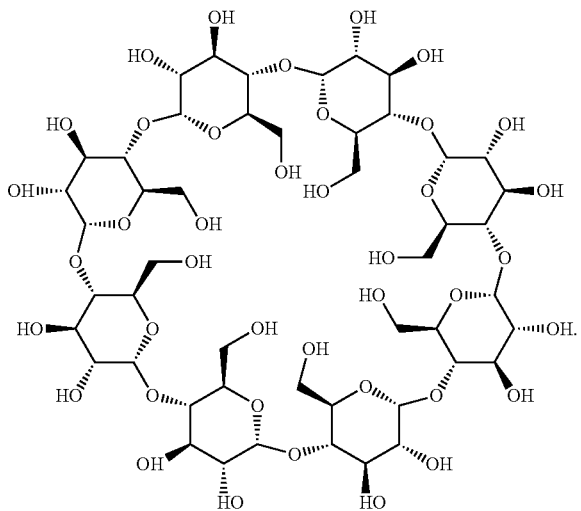 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]9[C@H](O)[C@@H](O)[C@@H](O[C@H]1[C@H](O)[C@H]2O)O[C@@H]9CO)O[C@@H]8CO)O[C@@H]7CO)O[C@@H]6CO)O[C@@H]5CO)O[C@@H]4CO)O[C@@H]3CO]

In some embodiments, the complex formed by the copper-containing peptide and the antioxidant is purple in color, while the copper-containing peptide is blue in color. In some embodiments, the complex formed by GHK-Cu peptide and carnosine is purple in color. In some embodiments, the complex formed by GHK-Cu peptide and L-carnosine is purple in color. In some embodiments, the composition is a blue-green color.

In some embodiments, the hair treatment composition and/or composition for treating an inflammatory skin condition has a pH between 5.5 and 7.3 (e.g., pH 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3 or any value therebetween). In some embodiments, the composition has a pH between band 7 (e.g., pH 6, 6.1, 6.2, 6.3, 6.4, 6.5, 6.6, 6.7, 6.8, 6.9, 7, or any value therebetween).

In some embodiments, the copper-containing peptide is entrapped by the cyclic oligosaccharide-based polymer. In some embodiments, the GHK-Cu peptide is entrapped by cyclodextrin. In some embodiments, the GHK-Cu peptide is entrapped by gamma cyclodextrin. In some embodiments, the complex formed by the copper-containing peptide and the antioxidant is entrapped by the cyclic oligosaccharide-based polymer. In some embodiments, the complex formed by GHK-Cu peptide and carnosine is entrapped by cyclodextrin. In some embodiments, the complex formed by GHK-Cu peptide and L-carnosine is entrapped by gamma cyclodextrin.

In some embodiments, the hair treatment composition and/or composition for treating an inflammatory skin condition comprises by weight of the total composition: (a) 0.05%-2% copper-containing peptide (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween); (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) antioxidant; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclic oligosaccharide-based polymer.

In some embodiments, the hair treatment composition and/or composition for treating an inflammatory skin condition comprises by weight of the total composition: (a) 0.05%-2% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) copper-containing peptide; (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) carnosine; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclodextrin.

In some embodiments, the hair treatment composition comprises by weight of the total composition: (a) 0.05%-2% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) GHK-Cu peptide; (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) L-carnosine; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) gamma cyclodextrin.

In some embodiments, the hair treatment composition further comprises at least one pharmaceutically acceptable carrier or excipient.

In some embodiments, the hair treatment composition further comprises at least one of: a pH buffer; a humectant; a nonionic surfactant; and a preservative.

In some embodiments, the hair treatment composition comprises 0.05%-3% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3%, or any value therebetween) pH buffer. In some embodiments, the hair treatment composition comprises 3%-30% (e.g., 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30%, or any value therebetween) humectant. In some embodiments, the hair treatment composition comprises 5%-15% (5, 5.5, 6, 6.5, 7, 7.5, 8, 8.5, 9, 9.5, 10, 10.5, 11, 11.5, 12, 12.5, 13, 13.5, 14, 14.5, 15%, or any value therebetween) nonionic surfactant. In some embodiments, the hair treatment composition comprises 0.05%-1.5% (e.g., 0.05, 0.1, 0.2, 0.3, 0.4, 0.5, 0.6, 0.7, 0.8, 0.9, 1, 1.1, 1.2, 1.3, 1.4, 1.5, or any value therebetween) preservative.

In some embodiments, the pH buffer comprises at least one of citric acid, magnesium citrate, magnesium sulfate, sodium citrate or sodium sulfate. In some embodiments, the pH buffer comprises citric acid.

In some embodiments, the humectant comprises at least one of an amino acid, aloe vera extract, a fatty acid, hyaluronic acid (HA), collagen, silicone, a disaccharide (e.g., sucrose or trehalose), maltitol, erythrol, sorbitol, glycerin, propanediol, propylene glycol, glycerin or any other glycol/diol. In some embodiments, the humectant comprises glycerin and/or HA. In some embodiments, HA is swapped for any other heavy molecular weight polymer such as collagen or a derivative. In some embodiments, collagen is interchangeable with HA or can be combined with HA, e.g., 0.6% HA combined with 0.5% collagen. In some embodiments, the composition comprises 0.2-5% of HA, 0.2-5% of collagen or derivatives thereof, or 0.2-5% of HA and collagen or a derivative thereof combined. In some embodiments, the composition comprises 3-30% (e.g., 3, 4, 5, 6, 7, 8, 9, 10, 11, 12, 13, 14, 15, 16, 17, 18, 19, 20, 21, 22, 23, 24, 25, 26, 27, 28, 29, 30% or any number therebetween) of propanediol, propylene glycol, glycerin or any other glycol/diol, or a combination thereof.

In some embodiments, the nonionic surfactant comprises at least one of tearyl alcohol, cetearyl alcohol, or a combination of both. In some embodiments, the nonionic surfactant comprises tearyl alcohol. In some embodiments, the nonionic surfactant comprises cetearyl alcohol. In some embodiments, the composition comprises 3-30% of a nonionic surfactant.

In some embodiments, the preservative comprises at least one of sodium benzoate, paraben, benzyl alcohol, sorbic acid, triclosan, phenoxyisopropanol, diazolidinyl urea, bronopol, Alkyl (C12-22) trimethyl ammonium bromide, Alkyl (C12-22) trimethyl ammonium chloride, Benzalkonium chloride, Benzalkonium bromide, Benzalkonium saccharinate, or phenoxyethanol. In some embodiments, the preservative comprises phenoxyethanol or ethylhexylglycerin or both, optionally at 0.5%-1.5% of the composition. In some embodiments, the phenoxyethanol or ethylhexylglycerin can be swapped for parabens or other aromatic alcohols such as benzyl alcohol, optionally at 0.5%-1.5% of the composition.

In some embodiments, the hair treatment composition further comprises at least one of the following constituents: sunflower oil, Tegomuls 90 S, cetyl alcohol, cetyl palmitate, Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

In some embodiments, the hair treatment composition further comprises at least one constituent selected from the group consisting of an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

In some embodiments, the composition is lyophilized. In some embodiments, the composition is spray dried to form a sterile powder. In some embodiments, the composition is freeze dried onto a patch.

In some embodiments, the hair treatment composition is a patch, a cream, an ointment, a powder, an aerosol spray, or a hydrogel. In some embodiments, the hair treatment composition is impregnated into a dressing.

In some embodiments, the hair treatment composition is administered topically.

In some embodiments, the hair treatment composition is administered every hour, every two hours, every three hours, every six hours, every twelve hours, every day, every two days, every three days, every five days, every seven days, every ten days, or every fourteen days.

In some embodiments, the methods of treating a hair condition as disclosed herein are effective to stimulate the rate of hair growth, stimulate the conversion of vellus hair or intermediate hair to growth as terminal hair, and combinations thereof. In some embodiments, the methods of treating a hair condition as disclosed herein are effective to prevent hair loss (such as on the scalp), treat hair loss, treat or thicken thinning hair, treat loss of eyebrows, treat loss of eyelashes, treat loss of facial or body hair, and combinations thereof. In some embodiments, the methods of treating a hair condition as disclosed herein are effective to treat all types of alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

In some embodiments, the method comprises administering a sunscreen in combination with the hair treatment composition, wherein the composition and the sunscreen can be administered simultaneous or sequentially.

The terminology used herein is for the purpose of describing particular embodiments only and is not intended to be limiting. As used in the specification and the appended claims, the singular forms "a," "an," and "the" include plural referents unless the context clearly dictates otherwise.

The following examples are provided to further illustrate the methods of the present invention. These examples are illustrative only and are not intended to limit the scope of the invention in any way.

EXAMPLES

Example 1: Composition for Use in Treatment of a Hair Condition

A hair treatment composition comprising the following ingredients was prepared: 2% Carnosine, 1% Histidine HCL, 0.2% GHK-Cu peptide, 0.5% Zinc pyrrolidone carboxylic acid (PCA), 0.5% Citric acid, 1% Gamma-Cyclodextrin, 2% Glycerin, 10% Propanediol, 0.7% Phenoxyethanol, 0.1% Ethylhexylglycerin, and 0.5% HA. The composition has a distinctive blue-green color at pH between 6 and 7 (FIG. 2); in contrast, the GHK-Cu peptide solution is blue in color (FIG. 1).

A second hair treatment composition comprising the following ingredients was also prepared: 4% Carnosine, 1% Histidine HCL, 0.2% GHK-Cu peptide, 0.5% Zinc PCA, 1% Citric acid, 1% Gamma-Cyclodextrin, 2% Glycerin, 10% Propanediol, 0.7% Phenoxyethanol, 0.1% Ethylhexylglycerin, and 0.5% HA.

Example 2: Gene Expression Analysis

A stock of Carnosine at 4% (meaning 177 mM) was made from a keratinocyte complete media and Fibroblast complete media at 1:1 ratio. The keratinocyte complete media is composed of Dermal Cell Basal Medium (ATCC, catalog #PCS-200-030) mixed with Keratinocyte Growth Kit (ATCC, catalog #PCS-200-040) as specified by ATCC. The Fibroblast complete media is composed of Eagle's Minimum Essential Medium (EMEM) (ATCC, catalog #30-2003) mixed with 10% of 53ecomplemented fetal bovine serum (Cytiva, catalog #SH30088.03) as specified by ATCC.

Primary adult normal Human Epidermal Keratinocytes (HEKa) (ATCC, catalog #PCS-200-011) were cultivated and expanded as a monoculture in complete Keratinocyte media; epidermal meaning from skin. Adult normal human skin fibroblasts (ATCC, catalog #CRL-2091) were cultivated and expanded as a monoculture in complete Fibroblast media.

When the experiments were set up, at that time only, both cells were cultivated together at a ratio of 1:1, using a media of complete Keratinocyte media and complete Fibroblast media at a ratio 1:1.

The experiments were used to identify biomarkers associated with hair growth on the co-culture of primary adult normal Epidermal Keratinocytes (HEKa) (ATCC, catalog #PCS-200-011) with adult normal skin fibroblasts (ATCC, catalog #CRL-2091). Both types of cells were plated at the same time and allowed to attach to the plate. After 24h, multiple co-cultures of cells were dosed with different concentrations of Carnosine, each condition in six replicates). After 24 hours of dosing, the media was discarded and fresh keratinocyte media/fibroblast media (1:1 ratio) without carnosine, was added to each co-culture condition. After an additional 24 hours the cells were lysed using lysis buffer (RLA with beta-mercaptoethanol) from a kit of total RNA extraction (SV Total RNA Isolation System) as specified by the vendor (Promega). Each condition and each replicate was extracted as a unique RNA sample.

After total RNA extraction, RNA was quantified and checked for quality by measuring the Optical Density of each individual RNA sample. A reverse transcription was performed on each individual RNA sample at 300 ng of total RNA using the SuperScript™ IV VILO™ Master Mix from vendor ThermoFisher Scientific following manufacturer instructions to produce a cDNA equivalent to each RNA sample in a machine used as a thermocycler.

After reverse transcription, each sample was diluted 1:1 with molecular biology grade water. After dilution of the cDNA samples, real-time PCR was performed on each cDNA sample (15 ng) set as multiplex, meaning two Tagmans were used simultaneously for each sample using a real-time PCR machine; one Taqman was the Eukaryotic 18S rRNA Endogenous Control the other Taqman was the target gene. The real-time PCR data is run as comparative Ct (delta delta Ct).

There was a new real-time PCR for each couple Eukaryotic 18S rRNA Endogenous Control the other Taqman was the target gene versus target gene Taqman. All target gene Taqmans were for human genes. Target genes were selected for genes known to play a role in hair growth. The different couples were as follows:

Eukaryotic 18S rRNA Endogenous Control Taqman (VIC™/MGB probe, primer limited, vendor # ThermoFisher Scientific, catalog #4319413E) and h TGF-3-2 (vendor # ThermoFisher Scientific, Assay ID #Hs00234244_m1);

Eukaryotic 18S rRNA Endogenous Control Taqman (VIC™/MGB probe, primer limited, vendor # ThermoFisher Scientific, catalog #4319413E) and h SDF-1 (vendor #ThermoFisher Scientific, Assay ID #Hs03676656_mH)

Eukaryotic 18S rRNA Endogenous Control Taqman (VIC™/MGB probe, primer limited, vendor #ThermoFisher Scientific, catalog #4319413E) and h AR (vendor #ThermoFisher Scientific, Assay ID #Hs00171172_m1)

Eukaryotic 18S rRNA Endogenous Control Taqman (VIC™/MGB probe, primer limited, vendor #ThermoFisher Scientific, catalog #4319413E) and h SRD5A1 (vendor #ThermoFisher Scientific, Assay ID #Hs00971645_g1)

Eukaryotic 18S rRNA Endogenous Control Taqman (VIC™/MGB probe, primer limited, vendor #ThermoFisher Scientific, catalog #4319413E) and h SRD5A3 (vendor #ThermoFisher Scientific, Assay ID #Hs00430680_g1)

Eukaryotic 18S rRNA Endogenous Control Taqman (VIC™/MGB probe, primer limited, vendor #ThermoFisher Scientific, catalog #4319413E) and h SRD5A2 (vendor #ThermoFisher Scientific, Assay ID #Hs00936406_m1)

Eukaryotic 18S rRNA Endogenous Control Taqman (VIC™/MGB probe, primer limited, ThermoFisher Scientific, catalog #4319413E) and h ACTA2 (ThermoFisher Scientific, Assay ID #Hs00426835_g1)

Eukaryotic 18S rRNA Endogenous Control Taqman (VIC™/MGB probe, primer limited, ThermoFisher Scientific, catalog #4319413E) and h HAVCR1 (ThermoFisher Scientific, Assay ID #Hs00930379_g1)

Eukaryotic 18S rRNA Endogenous Control Taqman (VIC™/MGB probe, primer limited, ThermoFisher Scientific, catalog #4319413E) and h IFN-g (ThermoFisher Scientific, Assay ID #Hs00989291_m1)

Eukaryotic 18S rRNA Endogenous Control Taqman (VIC™/MGB probe, primer limited, ThermoFisher Scientific, catalog #4319413E) and h ANG-2 (ThermoFisher Scientific, Assay ID #Hs00169867_m1)

Real-time PCR was analyzed as comparative Ct (delta delta Ct) using the Eukaryotic 18S rRNA Endogenous Control Taqman values as endogenous control, using Excel (Microsoft). T TEST (sample compared to control) was performed for the obtained data, with p value equal of less than 0.05 being considered significant.

Figure 3:
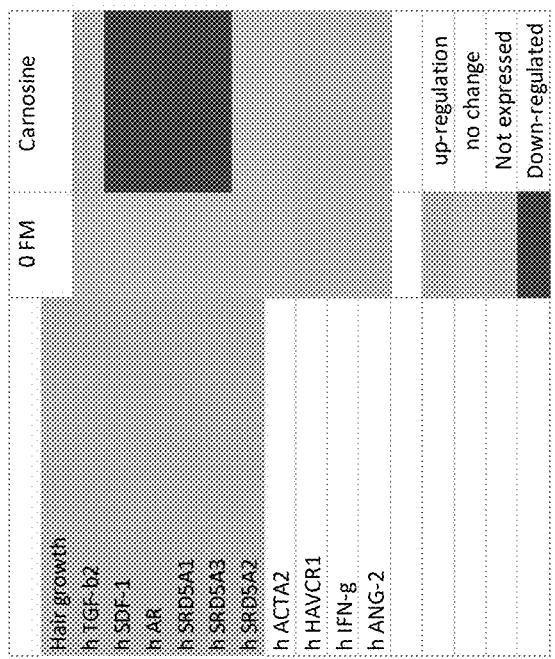
FIG. 3 shows the gene expression changes of human skin cells following treatment with carnosine, which is the main active ingredient of the composition according to certain embodiments disclosed herein.

The changes in gene expression observed after treatment are shown in FIG. 3.

Example 3: Human Testing of Hair Treatment Composition

Figure 4:
FIG. 4 shows an image of a human scalp/hair before and after treatment with a hair treatment composition as disclosed herein.

A hair treatment composition comprising the following ingredients was applied to the scalp of a human subject: 2% Carnosine, 1% Histidine HCL, 0.2% GHK-Cu peptide, 0.5% Zinc pyrrolidone carboxylic acid (PCA), 0.5% Citric acid, 1% Gamma-Cyclodextrin, 2% Glycerin, 10% Propanediol, 0.7% Phenoxyethanol, 0.1% Ethylhexylglycerin, and 0.5% HA. The hair treatment composition was applied 1 to 2 times per day for about 60 days. As shown in FIG. 4, after 60 days of treatment ("after" image) there is a surprising darkening of hair. Without being limited by theory, the hair treatment composition is effective to increase melanin expression (causing darkening) and regrowth of hair.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes can be made by those skilled in the art without departing from the spirit of this disclosure. Those skilled in the art will appreciate that the inventive principles can be practiced in other than the described embodiments, which are presented for purposes of illustration and not limitation.

Various Embodiments

Embodiment 1. A composition for use in treatment of a hair condition comprising:
(a) a copper-containing peptide;
(b) an antioxidant; and
(c) a cyclic oligosaccharide-based polymer,
wherein the copper-containing peptide and the antioxidant form a complex.

Embodiment 2. The composition of any preceding Embodiment, wherein the copper-containing peptide comprises glycyl-L-histidyl-L-lysine copper (GHK-Cu) peptide.

Embodiment 3. The composition of any preceding Embodiment, wherein the antioxidant comprises L-carnosine, D-carnosine, acetyl-carnosine, anserine, alanine, L-histidine, D-histidine, a derivative thereof, or a combination thereof.

Embodiment 4. The composition of any preceding Embodiment, wherein the antioxidant comprises L-carnosine.

Embodiment 5. The composition of any preceding Embodiment, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

Embodiment 6. The composition of any preceding Embodiment, wherein the cyclic oligosaccharide-based polymer comprises gamma cyclodextrin, optionally a non-crosslinked gamma cyclodextrin.

Embodiment 7. The composition of any preceding Embodiment, comprising GHK-Cu peptide, carnosine, and cyclodextrin.

Embodiment 8. The composition of any preceding Embodiment, comprising GHK-Cu peptide, L-carnosine, and gamma cyclodextrin.

Embodiment 9. The composition of any preceding Embodiment, wherein the complex formed by the copper-containing peptide and the antioxidant is purple in color.

Embodiment 10. The composition of any preceding Embodiment, wherein the composition has a pH between 5.5 and 7.3.

Embodiment 11. The composition of any preceding Embodiment, wherein the complex formed by the copper-containing peptide and the antioxidant is entrapped by the cyclic oligosaccharide-based polymer.

Embodiment 12. The composition of any preceding Embodiment, comprising by weight of the total composition: (a) 0.05%-2% copper-containing peptide; (b) 0.5%-10% antioxidant; and (c) 0.1%-20% cyclic oligosaccharide-based polymer.

Embodiment 13. The composition of any preceding Embodiment, comprising by weight of the total composition: (a) 0.05%-2% copper-containing peptide; (b) 0.5%-10% carnosine; and (c) 0.1%-20% cyclodextrin.

Embodiment 14. The composition of any preceding Embodiment, comprising by weight of the total composition: (a) 0.05%-2% GHK-Cu peptide; (b) 0.5%-10% L-carnosine; and (c) 0.1%-20% gamma cyclodextrin.

Embodiment 15. The composition of any preceding Embodiment, further comprising at least one pharmaceutically acceptable carrier or excipient.

Embodiment 16. The composition of any preceding Embodiment, wherein the composition is a patch, a cream, an ointment, a powder, an aerosol spray, or a hydrogel.

Embodiment 17. A method for treating a hair condition in a subject comprising administering to the subject in need thereof a therapeutically effective amount of a composition comprising:
(a) a copper-containing peptide;
(b) an antioxidant; and
(c) a cyclic oligosaccharide-based polymer, wherein the copper-containing peptide and the antioxidant form a complex.

Embodiment 18. The method of any preceding Embodiment, wherein the copper-containing peptide comprises glycyl-L-histidyl-L-lysine copper (GHK-Cu) peptide.

Embodiment 19. The method of any preceding Embodiment, wherein the antioxidant comprises L-carnosine, D-carnosine, acetyl-carnosine, anserine, alanine, L-histidine, D-histidine, a derivative thereof, or a combination thereof.

Embodiment 20. The method of any preceding Embodiment, wherein the antioxidant comprises L-carnosine.

Embodiment 21. The method of any preceding Embodiment, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

Embodiment 22. The method of any preceding Embodiment, wherein the cyclic oligosaccharide-based polymer comprises gamma cyclodextrin, optionally non-crosslinked gamma cyclodextrin.

Embodiment 23. The method of any preceding Embodiment, wherein the composition comprises GHK-Cu peptide, carnosine, and cyclodextrin.

Embodiment 24 The method of any preceding Embodiment, wherein the composition comprises GHK-Cu peptide, L-carnosine, and gamma cyclodextrin.

Embodiment 25. The method of any preceding Embodiment, wherein the complex formed by the copper-containing peptide and the antioxidant is purple in color.

Embodiment 26. The method of any preceding Embodiment, wherein the composition has a pH between 5.5 and 7.3.

Embodiment 27. The method of any preceding Embodiment, wherein the complex formed by the copper-containing peptide and the antioxidant is entrapped by the cyclic oligosaccharide-based polymer.

Embodiment 28. The method of any preceding Embodiment, wherein the composition comprises by weight of the total composition: (a) 0.05%-2% copper-containing peptide; (b) 0.5%-10% antioxidant; and (c) 0.1%-20% cyclic oligosaccharide-based polymer.

Embodiment 29. The method of any preceding Embodiment, wherein the composition comprises by weight of the total composition: (a) 0.05%-2% copper-containing peptide; (b) 0.5%-10% carnosine; and (c) 0.1%-20% cyclodextrin.

Embodiment 30. The method of any preceding Embodiment, wherein the composition comprises by weight of the total composition: (a) 0.05%-2% GHK-Cu peptide; (b) 0.5%-10% L-carnosine; and (c) 0.1%-20% gamma cyclodextrin.

Embodiment 31. The method of any preceding Embodiment, wherein the composition further comprises at least one pharmaceutically acceptable carrier or excipient.

Embodiment 32. The method of any preceding Embodiment, wherein the composition is a patch, a cream, an ointment, a powder, an aerosol spray, or a hydrogel.

Embodiment 33. The method of any preceding Embodiment, wherein the composition is administered topically.

Embodiment 34. The method of any preceding Embodiment, wherein the composition is administered every hour, every two hours, every three hours, every six hours, every twelve hours, every day, every two days, every three days, every five days, every seven days, every ten days, or every fourteen days.

Embodiment 35. The method of any preceding Embodiment, wherein the hair condition is alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

Embodiment 36. The method of any preceding Embodiment, wherein the composition is effective to treat male androgenetic alopecia (male pattern baldness).

Embodiment 37. The method of any preceding Embodiment, further comprising administering to the subject in need thereof a therapeutically effective amount of an additional therapeutic agents selected from the group consisting of minoxidil, Finasteride, and ketoconazole.

Embodiment 38. The method of any preceding Embodiment, further comprising administering a sunscreen.

Embodiment 39. A composition for altering gene expression of a cell in a human subject comprising:
(a) a copper-containing peptide;
(b) an antioxidant; and
(c) a cyclic oligosaccharide-based polymer,
wherein the copper-containing peptide and the antioxidant form a complex; and
wherein the composition is effective to decrease the gene expression of one or more of the genes hSDF-1, hAR, hSRD5A1, and hSRD5A3, and/or increase expression of TGF-β2.

Embodiment 40. The composition of any preceding Embodiment, wherein the copper-containing peptide comprises glycyl-L-histidyl-L-lysine copper (GHK-Cu) peptide.

Embodiment 41. The composition of any preceding Embodiment, wherein the antioxidant comprises L-carnosine, D-carnosine, acetyl-carnosine, anserine, alanine, L-histidine, D-histidine, a derivative thereof, or a combination thereof.

Embodiment 42. The composition of any preceding Embodiment, wherein the antioxidant comprises L-carnosine.

Embodiment 43. The composition of any preceding Embodiment, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

Embodiment 44. The composition of any preceding Embodiment, wherein the cyclic oligosaccharide-based polymer comprises gamma cyclodextrin.

Embodiment 45. The composition of any preceding Embodiment, wherein the gamma cyclodextrin is a non-crosslinked gamma cyclodextrin.

Embodiment 46. The composition of any preceding Embodiment, comprising GHK-Cu peptide, carnosine, and cyclodextrin.

Embodiment 47. The composition of any preceding Embodiment, comprising GHK-Cu peptide, L-carnosine, and gamma cyclodextrin.

Embodiment 48. The composition of any preceding Embodiment, wherein the complex formed by the copper-containing peptide and the antioxidant is purple in color.

Embodiment 49. The composition of any preceding Embodiment, wherein the composition has a pH between 5.5 and 7.3.

Embodiment 50. The composition of any preceding Embodiment, wherein the complex formed by the copper-containing peptide and the antioxidant is entrapped by the cyclic oligosaccharide-based polymer.

Embodiment 51. The composition of any preceding Embodiment, comprising by weight of the total composition: (a) 0.1%-2% copper-containing peptide; (b) 0.5%-10% antioxidant; and (c) 0.1%-20% cyclic oligosaccharide-based polymer.

Embodiment 52. The composition of any preceding Embodiment, comprising by weight of the total composition: (a) 0.1%-2% copper-containing peptide; (b) 0.5%-10% carnosine; and (c) 0.1%-20% cyclodextrin.

Embodiment 53. The composition of any preceding Embodiment, comprising by weight of the total composition: (a) 0.1%-2% GHK-Cu peptide; (b) 0.5%-10% L-carnosine; and (c) 0.1%-20% gamma cyclodextrin.

Embodiment 54. The composition of any preceding Embodiment, further comprising at least one pharmaceutically acceptable carrier or excipient.

Embodiment 55. The composition of any preceding Embodiment, wherein the composition is delivered by a patch, a cream, an ointment, a powder, an aerosol spray, or a hydrogel.

Embodiment 56. The composition of any preceding Embodiment, wherein the composition is effective to treat alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

Embodiment 57. The composition of any preceding Embodiment, wherein the hair condition is effective to treat male androgenetic alopecia (male pattern baldness).

Embodiment 58. A method for altering gene expression of a cell in a human subject comprising the steps of contacting the cell with a composition comprising:
(a) a copper-containing peptide;
(b) an antioxidant; and
(c) a cyclic oligosaccharide-based polymer,
wherein the copper-containing peptide and the antioxidant form a complex; and
wherein the gene expression is an decrease in one or more of the genes hSDF-1, hAR, hSRD5A1, and hSRD5A3, and/or an increase in expression of TGF-β2.

Embodiment 59. The method of any preceding Embodiment, wherein the copper-containing peptide comprises glycyl-L-histidyl-L-lysine copper (GHK-Cu) peptide.

Embodiment 60. The method of any preceding Embodiment, wherein the antioxidant comprises L-carnosine, D-carnosine, acetyl-carnosine, anserine, alanine, L-histidine, D-histidine, a derivative thereof, or a combination thereof.

Embodiment 61. The method of any preceding Embodiment, wherein the antioxidant comprises L-carnosine.

Embodiment 62. The method of any preceding Embodiment, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

Embodiment 63. The method of any preceding Embodiment, wherein the cyclic oligosaccharide-based polymer comprises gamma cyclodextrin.

Embodiment 64. The method of any preceding Embodiment, wherein the gamma cyclodextrin is a non-crosslinked gamma cyclodextrin.

Embodiment 65. The method of any preceding Embodiment, comprising GHK-Cu peptide, carnosine, and cyclodextrin.

Embodiment 66. The method of any preceding Embodiment, comprising GHK-Cu peptide, L-carnosine, and gamma cyclodextrin.

Embodiment 67. The method of any preceding Embodiment, wherein the complex formed by the copper-containing peptide and the antioxidant is purple in color.

Embodiment 68. The method of any preceding Embodiment, wherein the composition has a pH between 5.5 and 7.3.

Embodiment 69. The method of any preceding Embodiment, wherein the complex formed by the copper-containing peptide and the antioxidant is entrapped by the cyclic oligosaccharide-based polymer.

Embodiment 70. The method of any preceding Embodiment, comprising by weight of the total composition: (a) 0.1%-2% copper-containing peptide; (b) 0.5%-10% antioxidant; and (c) 0.1%-20% cyclic oligosaccharide-based polymer.

Embodiment 71. The method of any preceding Embodiment, comprising by weight of the total composition: (a) 0.1%-2% copper-containing peptide; (b) 0.5%-10% carnosine; and (c) 0.1%-20% cyclodextrin.

Embodiment 72. The method of any preceding Embodiment, comprising by weight of the total composition: (a) 0.1%-2% GHK-Cu peptide; (b) 0.5%-10% L-carnosine; and (c) 0.1%-20% gamma cyclodextrin.

Embodiment 73. The method of any preceding Embodiment, further comprising at least one pharmaceutically acceptable carrier or excipient.

Embodiment 74. The method of any preceding Embodiment, wherein the composition is delivered by a patch, a cream, an ointment, a powder, an aerosol spray, or a hydrogel.

Embodiment 75. The method of any preceding Embodiment, wherein the composition is effective to treat alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

Embodiment 76. The method of any preceding Embodiment, wherein the composition is effective to treat male androgenetic alopecia (male pattern baldness).

Embodiment 77. A kit for treating a hair condition, the kit comprising the composition of claim 1 and instructions for use thereof.

Embodiment 78. A kit for altering gene expression of a cell in a human subject, the kit comprising the composition of any preceding Embodiment and instructions for use thereof.

Embodiment 79. The composition of any preceding Embodiment, wherein the composition comprises a topical formulation suitable for application to the body surface selected from the group consisting of a cream, lotion, spray, solution, gel, ointment, paste, plaster, paint, bioadhesive, suspension, and emulsion.

Embodiment 80. The composition of any preceding Embodiment, wherein the composition comprises one or more of sunscreen, lotion, balm, shampoo, and moisturizer.

Embodiment 81. The composition of any preceding Embodiment, wherein the composition comprises one or more of sunscreen, lotion, balm, shampoo, and moisturizer.

Embodiment 82. The composition of any preceding Embodiment, wherein the composition comprises carnosine, Histidine HCL, GH-copper, zinc PCA, gamma cyclodextrin, glycerin, propanediol, phenoxyethanol, Ethylhexylglycerin, and HA.

Embodiment 83. The composition of any preceding Embodiment, wherein the composition comprises carnosine, Histidine HCL, GH-copper, zinc PCA, gamma cyclodextrin, glycerin, propanediol, phenoxyethanol, Ethylhexylglycerin, and HA.

Embodiment 84. The method of any preceding Embodiment, wherein the composition comprises carnosine, Histidine HCL, Gamma-cyclodextrin, GHK-copper peptide, Zinc PCA, and Aromatic alcohol (Benzyl alcohol or Phenoxyethanol).

Embodiment 85. The method of any preceding Embodiment, wherein the composition comprises carnosine, Histidine HCL, Gamma-cyclodextrin, GHK-copper peptide, Zinc PCA, and Aromatic alcohol (Benzyl alcohol or Phenoxyethanol).

Embodiment 86. The composition of any preceding Embodiment, wherein the composition comprises 2% L-carnosine, 1% L-Histidine HCL, 1% Gamma-cyclodextrin, 0.5% citric acid, 0.2% GHK-copper peptide, 0.2% Zinc PCA, and 0.5% Aromatic alcohol (Benzyl alcohol or Phenoxyethanol).

Embodiment 87. The composition of any preceding Embodiment, wherein the composition comprises 2% L-carnosine, 1% L-Histidine HCL, 1% Gamma-cyclodextrin, 0.5% citric acid, 0.2% GHK-copper peptide, 0.2% Zinc PCA, and 0.5% Aromatic alcohol (Benzyl alcohol or Phenoxyethanol).

Embodiment 88. The composition of any preceding Embodiment, wherein the composition comprises 2% carnosine, 1% Histidine HCL, 0.2% GH-copper, 0.5% zinc PCA, 0.5% citric acid, 1% gamma cyclodextrin, 2% glycerin, 10% propanediol, 0.7% phenoxyethanol, 0.1% Ethylhexylglycerin, and 0.5% HA.

Embodiment 89. The composition of any preceding Embodiment, wherein the composition comprises 2% carnosine, 1% Histidine HCL, 0.2% GH-copper, 0.5% zinc PCA, 0.5% citric acid, 1% gamma cyclodextrin, 2% glycerin, 10% propanediol, 0.7% phenoxyethanol, 0.1% Ethylhexylglycerin, and 0.5% HA.

Embodiment 90. The composition of any preceding Embodiment, wherein the composition comprises 4% carnosine, 1% Histidine HCL, 0.2% GH-copper, 0.5% zinc PCA, 1% citric acid, 1% gamma cyclodextrin, 2% glycerin, 10% propanediol, 0.7% phenoxyethanol, 0.1% Ethylhexylglycerin, and 0.5% HA.

Embodiment 91. The composition of any preceding Embodiment, wherein the composition comprises 4% carnosine, 1% Histidine HCL, 0.2% GH-copper, 0.5% zinc PCA, 1% citric acid, 1% gamma cyclodextrin, 2% glycerin, 10% propanediol, 0.7% phenoxyethanol, 0.1% Ethylhexylglycerin, and 0.5% HA.

Embodiment 92. The method of any preceding Embodiment, wherein the composition comprises 2% L-carnosine, 1% L-Histidine HCL, 1% Gamma-cyclodextrin, 0.5% citric acid, 0.2% GHK-copper peptide, 0.2% Zinc PCA, and 0.5% Aromatic alcohol (Benzyl alcohol or Phenoxyethanol).

Embodiment 93. The method of any preceding Embodiment, wherein the composition comprises 2% L-carnosine, 1% L-Histidine HCL, 1% Gamma-cyclodextrin, 0.5% citric acid, 0.2% GHK-copper peptide, 0.2% Zinc PCA, and 0.5% Aromatic alcohol (Benzyl alcohol or Phenoxyethanol).

Embodiment 94. The method of any preceding Embodiment, wherein the composition comprises 2% carnosine, 1% Histidine HCL, 0.2% GH-copper, 0.5% zinc PCA, 0.5% citric acid, 1% gamma cyclodextrin, 2% glycerin, 10% propanediol, 0.7% phenoxyethanol, 0.1% Ethylhexylglycerin, and 0.5% HA.

Embodiment 95. The method of any preceding Embodiment, wherein the composition comprises 2% carnosine, 1% Histidine HCL, 0.2% GH-copper, 0.5% zinc PCA, 0.5% citric acid, 1% gamma cyclodextrin, 2% glycerin, 10% propanediol, 0.7% phenoxyethanol, 0.1% Ethylhexylglycerin, and 0.5% HA.

Embodiment 96. The method of any preceding Embodiment, wherein the composition comprises 4% carnosine, 1% Histidine HCL, 0.2% GH-copper, 0.5% zinc PCA, 1% citric acid, 1% gamma cyclodextrin, 2% glycerin, 10% propanediol, 0.7% phenoxyethanol, 0.1% Ethylhexylglycerin, and 0.5% HA.

Embodiment 97. The method of any preceding Embodiment, wherein the composition comprises 4% carnosine, 1% Histidine HCL, 0.2% GH-copper, 0.5% zinc PCA, 1% citric acid, 1% gamma cyclodextrin, 2% glycerin, 10% propanediol, 0.7% phenoxyethanol, 0.1% Ethylhexylglycerin, and 0.5% HA.

Embodiment 98. The composition of any preceding Embodiment, further comprising an additional therapeutic agents selected from the group consisting of minoxidil, Finasteride, and ketoconazole.

Embodiment 99. The method of any preceding Embodiment, further comprising administering to the subject in need thereof a therapeutically effective amount of an additional therapeutic agents selected from the group consisting of minoxidil, Finasteride, and ketoconazole.

Embodiment 100. The composition of any preceding Embodiment, further comprising an additional therapeutic agents selected from the group consisting of minoxidil, Finasteride, and ketoconazole.

Embodiment 101. The method of any preceding Embodiment, further comprising administering to the subject in need thereof a therapeutically effective amount of an additional therapeutic agents selected from the group consisting of minoxidil, Finasteride, and ketoconazole.

Embodiment 102. The composition or method of any preceding Embodiment, wherein the composition comprises 24% carnosine, 1% Histidine HCL, 1% Gamma-cyclodextrin, 0.5-1% citric acid, 0.2% GHK-copper peptide, 0.2-0.5% Zinc PCA, 0.5-0.7% Aromatic alcohol (Benzyl alcohol or Phenoxyethanol), 0-2% glycerin, 0-10% propanediol, 0-0.1% Ethylhexylglycerin, and 0-0.5% HA.

What is claimed:

1. A composition for altering gene expression of a cell in a human subject comprising:
   (a) a glycyl-L-histidyl-L-lysine copper (GHK-Cu) peptide;
   (b) an antioxidant selected from the group consisting of L-carnosine, D-carnosine, acetyl-carnosine, and combinations thereof; and
   (c) a cyclodextran,
   wherein the GHK-Cu peptide and the antioxidant form a complex and the complex is entrapped by the cyclodextran; and
   wherein the composition is effective to decrease the gene expression of one or more of the genes hSDF-1, hAR, hSRD5A1, and hSRD5A3, and/or increase expression of TGF-β2.

2. The composition of claim 1, wherein the antioxidant further comprises anserine, alanine, L-histidine, D-histidine, a derivative thereof, or a combination thereof.

3. The composition of claim 1, wherein the cyclodextran comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

4. The composition of claim 1, comprising by weight of the total composition: (a) 0.1%-2% GHK-Cu peptide; (b) 0.5%-10% antioxidant; and (c) 0.1%-20% cyclodextran.

5. The composition of claim 1, wherein the composition is effective to treat alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

6. The composition of claim 1, wherein the composition comprises 2-4% carnosine, 1% Histidine HCL, 1% Gamma-cyclodextrin, 0.5-1% citric acid, 0.2% GHK-copper peptide, 0.2-0.5% Zinc PCA, 0.5-0.7% Aromatic alcohol (Benzyl alcohol or Phenoxyethanol), 0-2% glycerin, 0-10% propanediol, 0-0.1% Ethylhexylglycerin, and 0-0.5% HA.

7. The composition of claim 1, wherein the composition comprises a topical formulation suitable for application to the body surface selected from the group consisting of a cream, lotion, spray, solution, gel, ointment, paste, plaster, paint, bioadhesive, suspension, and emulsion.

8. A composition for use in treatment of a hair condition comprising:
   (a) a glycyl-L-histidyl-L-lysine copper (GHK-Cu) peptide;
   (b) an antioxidant selected from the group consisting of L-carnosine, D-carnosine acetyl-carnosine, and combinations thereof; and
   (c) a cyclodextran,
   wherein the GHK-Cu peptide and the antioxidant form a complex and the complex is entrapped by the cyclodextran.

9. The composition of claim 8, wherein the antioxidant further comprises anserine, alanine, L-histidine, D-histidine, a derivative thereof, or a combination thereof.

10. The composition of claim 8, wherein the cyclodextran comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

11. The composition of claim 8, comprising by weight of the total composition: (a) 0.05%-2% GHK-Cu peptide; (b) 0.5%-10% antioxidant; and (c) 0.1%-20%.

12. The composition of claim 8, further comprising an additional therapeutic agent selected from the group consisting of minoxidil, Finasteride, and ketoconazole.

13. The composition of claim 8, wherein the composition is a patch, a cream, an ointment, a powder, an aerosol spray, or a hydrogel.

14. The composition of claim 8, wherein the composition comprises 2-4% carnosine, 1% Histidine HCL, 1% Gamma-cyclodextrin, 0.5-1% citric acid, 0.2% GHK-copper peptide, 0.2-0.5% Zinc PCA, 0.5-0.7% Aromatic alcohol (Benzyl alcohol or Phenoxyethanol), 0-2% glycerin, 0-10% propanediol, 0-0.1% Ethylhexylglycerin, and 0-0.5% HA.

15. A method for treating a hair condition in a subject comprising administering to the subject in need thereof a therapeutically effective amount of a composition comprising:
(a) a glycyl-L-histidyl-L-lysine copper (GHK-Cu) peptide;
(b) an antioxidant selected from the group consisting of L-carnosine, D-carnosine, acetyl-carnosine, and combinations thereof; and
(c) a cyclodextran, wherein the GHK-Cu peptide and the antioxidant form a complex and the complex is entrapped by the cyclic oligosaccharide-based polymer.

16. The method of claim 15, wherein the antioxidant further comprises anserine, alanine, L-histidine, D-histidine, a derivative thereof, or a combination thereof.

17. The method of claim 15, wherein the cyclodextran comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

18. The method of claim 15, wherein the composition comprises by weight of the total composition: (a) 0.05%-2% GHK-Cu peptide; (b) 0.5%-10% antioxidant; and (c) 0.1%-20%.

19. The method of claim 15, wherein the hair condition is alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

20. The method of claim 15, further comprising administering to the subject in need thereof a therapeutically effective amount of an additional therapeutic agents selected from the group consisting of minoxidil, Finasteride, and ketoconazole.

21. A method for altering gene expression of a cell in a human subject comprising the steps of contacting the cell with a composition comprising:
(a) a glycyl-L-histidyl-L-lysine copper (GHK-Cu) peptide;
(b) an antioxidant selected from the group consisting of L-carnosine, D-carnosine, acetyl-carnosine, and combinations thereof, and
(c) a cyclodextran,
wherein the GHK-Cu peptide and the antioxidant form a complex and the complex is entrapped by the cyclodextran; and
wherein the gene expression is a decrease in one or more of the genes hSDF-1, hAR, hSRD5A1, and hSRD5A3, and/or an increase in expression of TGF-β2.

22. The method of claim 21, wherein the antioxidant further comprises anserine, alanine, L-histidine, D-histidine, a derivative thereof, or a combination thereof.

23. The method of claim 21, wherein the cyclodextran comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

24. The method of claim 21, comprising by weight of the total composition: (a) 0.1%-2% GHK-Cu peptide; (b) 0.5%-10% antioxidant; and (c) 0.1%-20% cyclodextran.

25. The method of claim 21, wherein the composition is delivered by a patch, a cream, an ointment, a powder, an aerosol spray, or a hydrogel.

26. The method of claim 15, wherein the composition is effective to treat alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

* * * * *

UNITED STATES PATENT AND TRADEMARK OFFICE
CERTIFICATE OF CORRECTION

PATENT NO. : 12,409,204 B1  
APPLICATION NO. : 18/600574  
DATED : September 9, 2025  
INVENTOR(S) : Jacob J. Miguel, Spencer Bouhadir and Jacob A. Miguel Page 1 of 1

It is certified that error appears in the above-identified patent and that said Letters Patent is hereby corrected as shown below:

In the Claims

Claim 1, Column 38, Line 16 the word 'cyclodextran' should read -cyclodextrin-.

Claim 1, Column 38, Line 18 the word 'cyclodextran' should read -cyclodextrin-.

Claim 3, Column 38, Line 27 the word 'cyclodextran' should read -cyclodextrin-.

Claim 4, Column 38, Line 34 the word 'cyclodextran' should read -cyclodextrin-.

Claim 8, Column 38, Line 65 the word 'cyclodextran' should read -cyclodextrin-.

Claim 8, Column 38, Line 67 the word 'cyclodextran' should read -cyclodextrin-.

Claim 10, Column 39, Line 4 the word 'cyclodextran' should read -cyclodextrin-.

Claim 15, Column 39, Line 33 the word 'cyclodextran' should read -cyclodextrin-.

Claim 17, Column 39, Line 39 the word 'cyclodextran' should read -cyclodextrin-.

Claim 21, Column 40, Line 20 the word 'cyclodextran' should read -cyclodextrin-.

Claim 21, Column 40, Line 22 the word 'cyclodextran' should read -cyclodextrin-.

Claim 23, Column 40, Line 30 the word 'cyclodextran' should read -cyclodextrin-.

Claim 24, Column 40, Line 37 the word 'cyclodextran' should read -cyclodextrin-.

Signed and Sealed this  
Thirteenth Day of January, 2026

John A. Squires  
*Director of the United States Patent and Trademark Office*